United States Patent
Centen

(10) Patent No.: US 9,585,603 B2
(45) Date of Patent: *Mar. 7, 2017

(54) CPR ASSIST DEVICE FOR MEASURING COMPRESSION PARAMETERS DURING CARDIOPULMONARY RESUSCITATION

(75) Inventor: Corey Centen, Ottawa (CA)

(73) Assignee: Physio-Control Canada Sales Ltd., Mississauga, Ontario (CA)

(*) Notice: Subject to any disclaimer, the term of this patent is extended or adjusted under 35 U.S.C. 154(b) by 1744 days.

This patent is subject to a terminal disclaimer.

(21) Appl. No.: 12/354,913

(22) Filed: Jan. 16, 2009

(65) Prior Publication Data

US 2010/0022904 A1    Jan. 28, 2010

Related U.S. Application Data

(63) Continuation-in-part of application No. 12/190,881, filed on Aug. 13, 2008, now abandoned.

(Continued)

(51) Int. Cl.
*A61B 5/08*    (2006.01)
*A61B 5/11*    (2006.01)
(Continued)

(52) U.S. Cl.
CPC ........... *A61B 5/1114* (2013.01); *A61B 5/1135* (2013.01); *A61B 5/6833* (2013.01); *A61B 5/7203* (2013.01); *A61H 31/005* (2013.01); *A61H 31/007* (2013.01); *A61N 1/0492* (2013.01); *A61N 1/362* (2013.01); *A61N 1/39* (2013.01); *G01B 7/004* (2013.01); *G09B 23/288* (2013.01); *A61B 5/6824* (2013.01);
(Continued)

(58) Field of Classification Search
CPC ..... A61N 1/362; A61N 1/39; A61H 2205/084

USPC ....... 600/301, 481, 529, 534; 607/5; 601/41; 324/207.16, 207.17, 207.24
See application file for complete search history.

(56) References Cited

U.S. PATENT DOCUMENTS 4,122,427 A * 10/1978 Karsh ............................ 367/89
4,945,305 A    7/1990 Blood
(Continued)

FOREIGN PATENT DOCUMENTS

EP    1516583 A2    3/2005
EP    1859770 A1    11/2007
(Continued)

OTHER PUBLICATIONS

International Search Report, Jan. 28, 2010, 5 pages, PCT/CA2009/000045, Canadian Intellectual Property Office, Gatineau, Quebec.
(Continued)

*Primary Examiner* — Jacqueline Cheng
*Assistant Examiner* — Puya Agahi
(74) *Attorney, Agent, or Firm* — Lane Powell PC

(57) ABSTRACT

A device for the determination of at least one compression parameter during administration of cardiopulmonary resuscitation (CPR) on a patient comprising: a field generator, a field detector, and a processor. Position information and the compression parameter are determined from the field detected by the field detector. One of the field generator and the field detector is a position sensor and the other is a reference sensor.

41 Claims, 24 Drawing Sheets

Related U.S. Application Data

(60) Provisional application No. 61/082,878, filed on Jul. 23, 2008, provisional application No. 61/103,132, filed on Oct. 6, 2008.

(51) Int. Cl.
| | | |
|---|---|---|
| *A61N 1/362* | (2006.01) | |
| *A61H 31/00* | (2006.01) | |
| *A61N 1/39* | (2006.01) | |
| *G01B 7/004* | (2006.01) | |
| *G09B 23/28* | (2006.01) | |
| *A61B 5/113* | (2006.01) | |
| *A61N 1/04* | (2006.01) | |
| *A61B 5/00* | (2006.01) | |

(52) U.S. Cl.
CPC ... *A61B 2505/01* (2013.01); *A61B 2560/0214* (2013.01); *A61B 2560/0252* (2013.01); *A61H 2201/5064* (2013.01); *A61H 2201/5071* (2013.01); *A61H 2201/5082* (2013.01); *A61H 2201/5097* (2013.01); *A61H 2205/084* (2013.01); *A61N 1/046* (2013.01); *A61N 1/3925* (2013.01); *A61N 1/3993* (2013.01)

(56) References Cited

U.S. PATENT DOCUMENTS

| | | | | |
|---|---|---|---|---|
| 5,307,072 | A * | 4/1994 | Jones, Jr. | F41G 3/08 324/244 |
| 5,831,260 | A * | 11/1998 | Hansen | 250/221 |
| 6,269,262 | B1 * | 7/2001 | Kandori et al. | 600/409 |
| 6,306,107 | B1 | 10/2001 | Myklebust et al. | |
| 6,351,671 | B1 | 2/2002 | Myklebust et al. | |
| 6,369,564 | B1 * | 4/2002 | Khalfin | G01B 3/1084 324/207.12 |
| 7,074,199 | B2 | 7/2006 | Halperin et al. | |
| 7,122,014 | B2 | 10/2006 | Palazzolo et al. | |
| 7,220,235 | B2 * | 5/2007 | Geheb et al. | 601/41 |
| 7,402,996 | B2 | 7/2008 | Arai et al. | |
| 7,918,801 | B2 * | 4/2011 | Cochran | 600/534 |
| 2004/0071337 | A1 * | 4/2004 | Jeung et al. | 382/151 |
| 2004/0115607 | A1 * | 6/2004 | Pastrick et al. | 434/262 |
| 2004/0116786 | A1 * | 6/2004 | Iijima et al. | 600/301 |
| 2004/0122334 | A1 * | 6/2004 | Yamashiro | 600/534 |
| 2004/0210172 | A1 * | 10/2004 | Palazzolo et al. | 601/41 |
| 2004/0267325 | A1 * | 12/2004 | Geheb et al. | 607/5 |
| 2005/0052178 | A1 * | 3/2005 | Ries | 324/207.23 |
| 2005/0267536 | A1 * | 12/2005 | Freeman et al. | 607/5 |
| 2006/0004281 | A1 * | 1/2006 | Saracen | A61B 5/1127 600/414 |
| 2006/0247560 | A1 | 11/2006 | Halperin et al. | |
| 2007/0010764 | A1 | 1/2007 | Palazzolo et al. | |
| 2007/0135739 | A1 | 6/2007 | Halperin et al. | |
| 2007/0167722 | A1 * | 7/2007 | Bladen et al. | 600/407 |
| 2007/0186429 | A1 * | 8/2007 | Bonnet | A61B 5/1116 33/512 |
| 2007/0276300 | A1 | 11/2007 | Olson et al. | |
| 2008/0053445 | A1 * | 3/2008 | Kroupa et al. | 128/205.23 |
| 2008/0146973 | A1 | 6/2008 | Lund et al. | |
| 2008/0171311 | A1 | 7/2008 | Centen et al. | |
| 2008/0208082 | A1 * | 8/2008 | Nysaether et al. | 600/595 |
| 2008/0242956 | A1 * | 10/2008 | Suzuki et al. | 600/301 |
| 2008/0248871 | A1 * | 10/2008 | Szturm | G06F 3/0346 463/36 |
| 2008/0287751 | A1 * | 11/2008 | Stivoric et al. | 600/301 |
| 2008/0306355 | A1 * | 12/2008 | Walker | 600/301 |
| 2009/0112135 | A1 * | 4/2009 | Palazzolo et al. | 601/41 |

FOREIGN PATENT DOCUMENTS

| | | |
|---|---|---|
| EP | 1057451 A2 | 1/2009 |
| WO | 9605768 A1 | 2/1996 |
| WO | 0017603 A1 | 3/2000 |
| WO | 2004037154 A2 | 5/2004 |
| WO | 2007057825 A2 | 5/2007 |
| WO | 2008015624 A2 | 2/2008 |
| WO | 2008059394 A1 | 5/2008 |

OTHER PUBLICATIONS

International Preliminary Report on Patentability, Jan. 23, 2011, 4 pages, PCT/CA2009/000045, Canadian Intellectual Property Office, Gatineau, Quebec.

Written Opinion of the International Searching Authority, Mar. 10, 2009, 4 pages, PCT/CA2009/000045, Canadian Intellectual Property Office, Gatineau, Quebec.

Extended European Search Report for European Patent Application No. 09799884.3, dated Apr. 17, 2015, 7 pages, Munich.

\* cited by examiner $$Y = \begin{bmatrix} a_1 & a_2 & a_3 \\ b_1 & b_2 & b_3 \\ c_1 & c_2 & c_3 \end{bmatrix}$$

FIG. 10

CPR ASSIST DEVICE FOR MEASURING COMPRESSION PARAMETERS DURING CARDIOPULMONARY RESUSCITATION

CROSS-REFERENCE TO RELATED APPLICATION

This disclosure claims priority from U.S. Provisional Application No. 61/082,878, filed Jul. 23, 2008; and U.S. Provisional Application No. 61/103,132, filed Oct. 6, 2008, the disclosures of which are hereby incorporated by reference in their entirety. This disclosure is a continuation-in-part of U.S. patent application Ser. No. 12/190,881, filed Aug. 13, 2008.

TECHNICAL FIELD

This disclosure relates to the measurement of compression parameters during the administration of cardiopulmonary resuscitation (CPR). In particular, this disclosure relates to measurement of compression parameters by use of a position sensor and a reference sensor.

BACKGROUND

There are currently an estimated 40,000 incidences of cardiac arrest every year in Canada, most of which take place outside of hospital settings. The odds of an out-of-hospital cardiac arrest currently stand at approximately 5%. In the U.S., there are about 164,600 such instances each year, or about 0.55 per 1000 population. It may be desirable to decrease the number of deaths resulting from these out-of-hospital incidences of cardiac arrest. Certain places, such as sports arenas, and certain individuals, such as the elderly, are at particular risk and in these places and for these people, a convenient solution may be the difference between survival and death.

Cardiopulmonary resuscitation (CPR) is a proven effective technique for medical and non-medical professionals to improve the chance of survival for patients experiencing cardiac failure. CPR forces blood through the circulatory system until professional medical help arrives, thereby maintaining oxygen distribution throughout the patient's body. However, the quality of CPR is often poor. Retention of proper CPR technique and protocol may be inadequate in most individuals and the anxiety of an emergency situation may confuse and hinder an individual in delivering proper treatment.

According to the Journal of the American Medical Association (2005), cardiopulmonary resuscitation (CPR) is often performed inconsistently and inefficiently, resulting in preventable deaths. Months after the completion of standard CPR training and testing, an individual's competency at performing effective chest compressions often deteriorates significantly. This finding was found to hold true for untrained performers as well as trained professionals such as paramedics, nurses, and even physicians.

The International Liaison Committee on Resuscitation in 2005 described an effective method of administering CPR and the parameters associated with an effective technique. Parameters include chest compression rate and chest compression depth. Chest compression rate is defined as the number of compressions delivered per minute. Chest compression depth is defined as how far the patient's sternum is displaced by each compression. An effective compression rate may be 100 chest compressions per minute at a compression depth of about 4-5 cm. According to a 2005 study of actual CPR administration at Ulleval University Hospital in Norway, on average, compression rates were less than 90 compressions per minute and compression depth was too shallow for 37% of compressions.

According to the same study, CPR was often administered when unnecessary or was not administered when necessary. The study found that compressions were not delivered 48% of the time when cardiovascular circulation was absent.

Other studies have found similar deficiencies in the delivery of CPR. One 2005 study at the University of Chicago found that 36.9% of the time, less than 80 compressions per minute where given, and 21.7% of the time, less than 70 compressions per minute were given. The chest compression rate was found to directly correlate to the spontaneous return of circulation after cardiac arrest.

In addition to too shallow compressions, too forceful compressions may also be problematic. Some injuries related to CPR are injury to the patient in the form of cracked ribs or cartilage separation. Such consequences may be due to excessive force or compression depth. Once again, lack of practice may be responsible for these injuries.

Positioning of the hands is another parameter that may be considered when delivering CPR. It has been found that an effective position for the hands during compression is approximately two inches above the base of the sternum. Hand positioning for effective CPR may be different depending on the patient. For example, for performing CPR on an infant, an effective position may be to use two fingers over the sternum.

Therefore, a device to facilitate the proper delivery of CPR in an emergency may be useful. Furthermore, a device that can also be used in objectively training and testing an individual may be useful for the CPR training process and protocol retention.

There are currently mechanical systems for the delivery of CPR that may be used in a hospital setting. Chest compressions may be delivered through a mechanism comprising mechanical movement (e.g., piston movement or motor movement). One such device is the AutoPulse™ by Revivant Corp, which has a computer-controlled motor attached to a wide chest band that compresses the patient's chest, forcing blood to the brain when the heart has stopped beating. Such a device is cumbersome and heavy to transport, requires time to set up and activate, and is expensive. Such devices have shown inconclusive results in studies trying to determine their effectiveness at increasing survival rates from cardiac arrest.

U.S. Pat. No. 6,351,671 discloses a device that measures the chest impedance of a patient as well as the force of active chest compressions. From these calculations, the device indicates to the user when a successful compression has been completed. However, this technology requires defibrillator pads to be placed across the chest of the patient and is, consequently, relatively time consuming to activate. The commercially available device, Q-CPR® by Phillips Medical, must be attached to an expensive hospital-grade defibrillator making it expensive, heavy and inaccessible to the lay user. Furthermore, this technology relies heavily on data collected from an accelerometer. Many current technologies are based around accelerometer technology.

Another device using accelerometer technology for the determination of compression depth is disclosed in U.S. Pat. No. 7,074,199. Any acceleration data from accelerometers used to measure the depth of chest compression during CPR is prone to cumulative errors and drift errors. Consequently, these sensors are not suitable for highly accurate or detailed data collection regarding CPR parameters and can only be relied on for approximate depth values. Furthermore, the use of an accelerometer in a CPR monitoring device without an external reference is prone to error if the patient or rescuer is mobile. For example, if the patient is being medically transported in an ambulance, helicopter or on a gurney, the accelerometer is unable to differentiate between the external movement of the patient and the compressions of the chest. In any type of non-stationary environment, an accelerometer based device may be unreliable and ineffective. The use of an accelerometer to calculate compression depth also relies on complicated and error-prone calculations to compensate for the angle and tilt of the compression device. If the accelerometer is not perfectly level on the chest of the patient and its movement is not perfectly vertical, errors may accumulate and must be accounted for by the angle of the two horizontal axes. Furthermore, the absence of any external reference point makes it difficult for the device to know its position in space at any given time. All measurements of distance are relative and an origin of movement is difficult to ascertain and maintain over the course of measurements. This may cause the initiation or starting point of the compressions to drift over time leading to errors in depth measurements. Certain commercial products currently use accelerometer technology, such as the AED Plus® D-Padz® from Zoll Medical, in which the accelerometer is embedded into the pads of the defibrillator. Due to the additional circuitry and sensory within them, these defibrillator pads are substantially more expensive and must be disposed of after each use. Therefore, relatively expensive sensory must be routinely discarded due to the design of the product.

U.S. Patent Application Publication No. 2007/0276300 to Kenneth F. Olson et al. discloses a device using ultrasound transmission to calculate compression depth. An acoustic signal is transmitted from a device on the chest of the patient to a receiver in another location. This device has several drawbacks. First, the ultrasound signal must have a clear line of sight from transmitter to receiver in order to operate. Any interference, objects, people or even the hand of the rescuer in the way of the signal may result in signal loss or deterioration. The transmitter must be directed toward the receiver and the relative orientation between the transmitter and receiver is crucial. Second, ultrasound is relatively slow and a time-of-flight measurement of an ultrasound signal may suffer from significant lag and latency. Third, an ultrasound signal is highly dependent on ambient conditions such as air temperature. If air temperature fluctuates, so does the speed of sound, which may result in inaccuracies. Finally, if the plane of the chest compression is initially unknown, the calculation of compression depth may be significantly compromised. Time-of-flight ultrasonic distance interpolation cannot resolve the position of the receiver in six degrees of freedom and the determination of the downward translational movement if the patient, receiver or transmitter is not level may be difficult. Even if ultrasonic triangulation is employed, latency may be significant, resolution may be low and multiple transmitters and receivers in different locations may be required.

It may be desirable to provide an easy-to-use and inexpensive device to accurately measure relevant CPR parameters such as compression depth and rate absent of the problems in the aforementioned technologies. Additionally, it may be useful for the device to provide instructions for carrying out CPR procedure for training, testing, and/or emergency situations.

SUMMARY

The present disclosure is directed to a method and device for determination of compression parameters during administration of CPR. The device may also be referred to as a CPR assist device. The device includes a transmitter sensor and a receiver sensor, which may specifically be a field generator and a field detector, respectively. The generator and detector may be used as a reference sensor and a position sensor. The reference sensor is relatively stationary, while the position sensor moves according to each chest compression.

The use of a fixed reference sensor and a position sensor may be advantageous over existing technologies currently employed for the determination of chest compression depth during the administration of CPR. Current methods of compression depth determination employing accelerometers may have errors resulting from signal drift. Furthermore, accelerometer based systems are typically sensitive to movements external to the chest compression. An accelerometer uses the Earth as its reference and thus, if the patient is transported, for example on a gurney, ambulance or helicopter, these external movements may influence or corrupt the measurements of chest compression depth. Furthermore, accelerometers are typically susceptible to various sources of noise and the use of double integration to obtain displacement from acceleration introduces various errors into the measurements. The use of a reference sensor and a position sensor, as in the present device and method, eliminates these problems. Various technologies, such as electromagnetic coils, enable measurements of significantly higher accuracy with little or no drift in the signal.

In some aspects, there is provided a device for the determination of at least one compression parameter during administration of cardiopulmonary resuscitation (CPR) on a patient comprising: a field generator adapted to generate a field; a field detector adapted to detect the field generated by the field generator and generate a response signal; and a processor adapted to determine from the response signal position information for the field detected relative to the field generator, and to determine the at least one compression parameter using the determined position information of the field detector; wherein one of the field generator and the field detector is a position sensor adapted to move in accordance with a patient's chest and the other of the field generator and the field detector is a reference sensor adapted to be stationary relative to the patient.

In some aspects, there is provided a method for determining at least one compression parameter during administration of cardiopulmonary resuscitation (CPR), the method comprising: providing the device described above; determining the position of the position sensor relative to the reference sensor; and determining the at least one compression parameter based on the determined position of the position sensor.

BRIEF DESCRIPTION OF THE DRAWINGS

Aspects of the present disclosure will be discussed in detail below, with reference to the drawings in which:

FIG. 10 is a diagram illustrating an example of a matrix containing information from detected fields in an embodiment of the CPR assist device;

DETAILED DESCRIPTION

The present disclosure is directed to a method and device for the determination and calculation of chest compression parameters during the administration of cardiopulmonary resuscitation (CPR). The device may also be referred to as a CPR assist device.

The device includes a transmitter sensor and a receiver sensor, which may more specifically be a field generator and a field detector, respectively. Unlike a general transmitter sensor and receiver sensor, a field generator and field detector specifically generates and detects a field, such as an electromagnetic field, rather than simply transmitting and receiving a simple directed signal. In contrast to simple signal transmission (e.g. infrared light, ultrasound), the generated field occupies a spherical zone around the field generator that is not obstructed or blocked by objects in the zone. Rather than a directed singular beam or path, as in the case of a transmitted signal, the field is simultaneously present at all points around the field generator within a given radius. Certain transmitted signals require a direct line-of-sight between transmitter and receiver (i.e., there must be no obstruction between the transmitter and the sensor), but the field generated by the field generator described here does not has this limitation. Furthermore, in using simple transmitted signals, the distance between the transmitter and the snsor must be calculated based on unreliable data such as time-of-flight of the signal. For example, an ultrasound time-of-flight measurement is sensitive to properties of the transmission medium such as air temperature. Such a limitation is not encountered in generated fields as described here.

In some embodiments, the field detector is a position sensor and the field generator is a reference sensor. The position sensor may be placed at a location that corresponds to movement of the patient's chest, while the reference sensor may be placed at a relatively stationary location. Signals, for example electromagnetic fields, are generated by the reference sensor and detected by the position sensor. In other embodiments, the field detector is the reference sensor and the field generator is the position sensor, in which case signals, which may be fields, are generated by the position sensor and detected by the reference sensor. It would be clear to a skilled person that the position sensor and reference sensor are interchangeable. A processor in the device determines the position of the position sensor relative to the reference sensor based on the signal. Based on the determined position, the processor determines the chest compression depth during administration of CPR.

Figure 1:
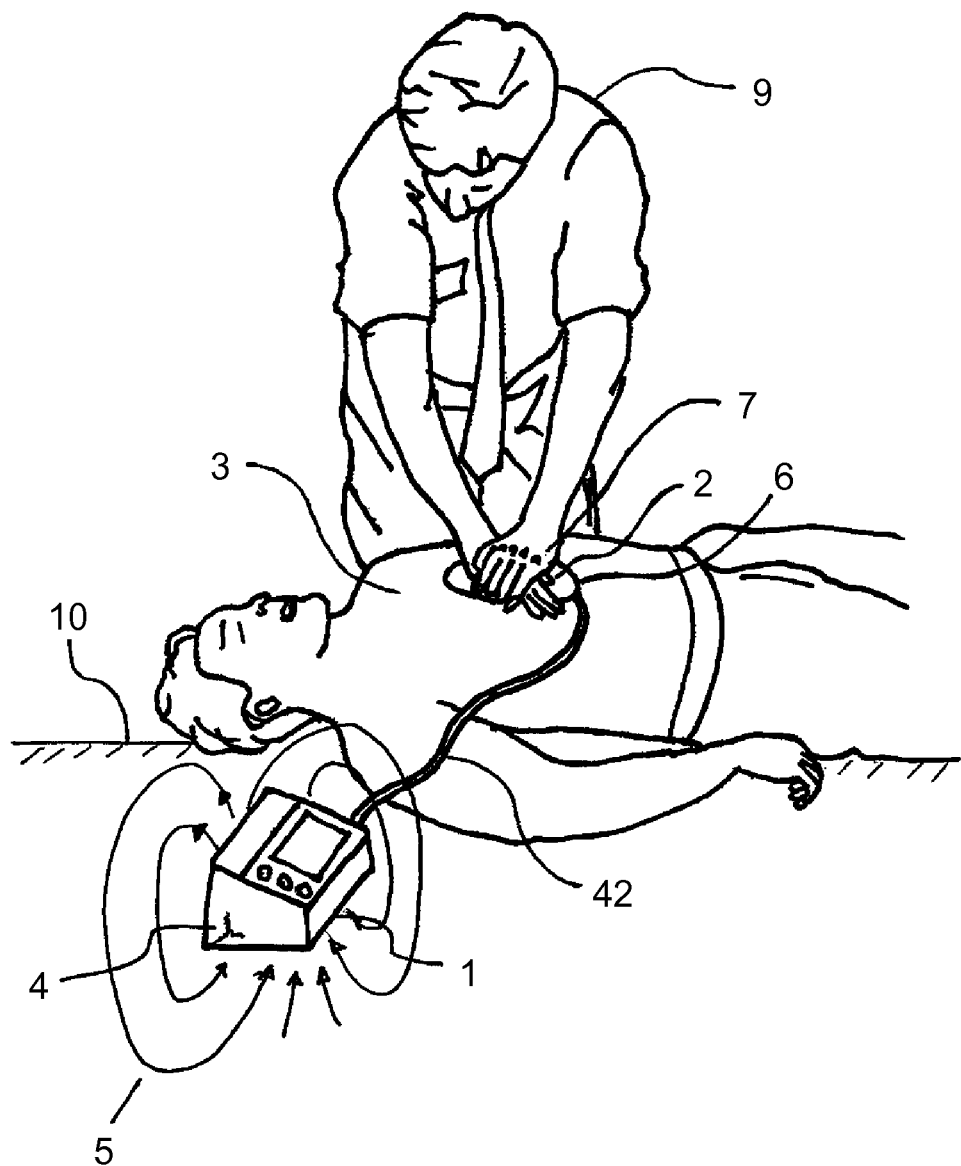
FIG. 1 is an illustration of a CPR assist device in accordance with an embodiment of the present disclosure.
Figure 2:
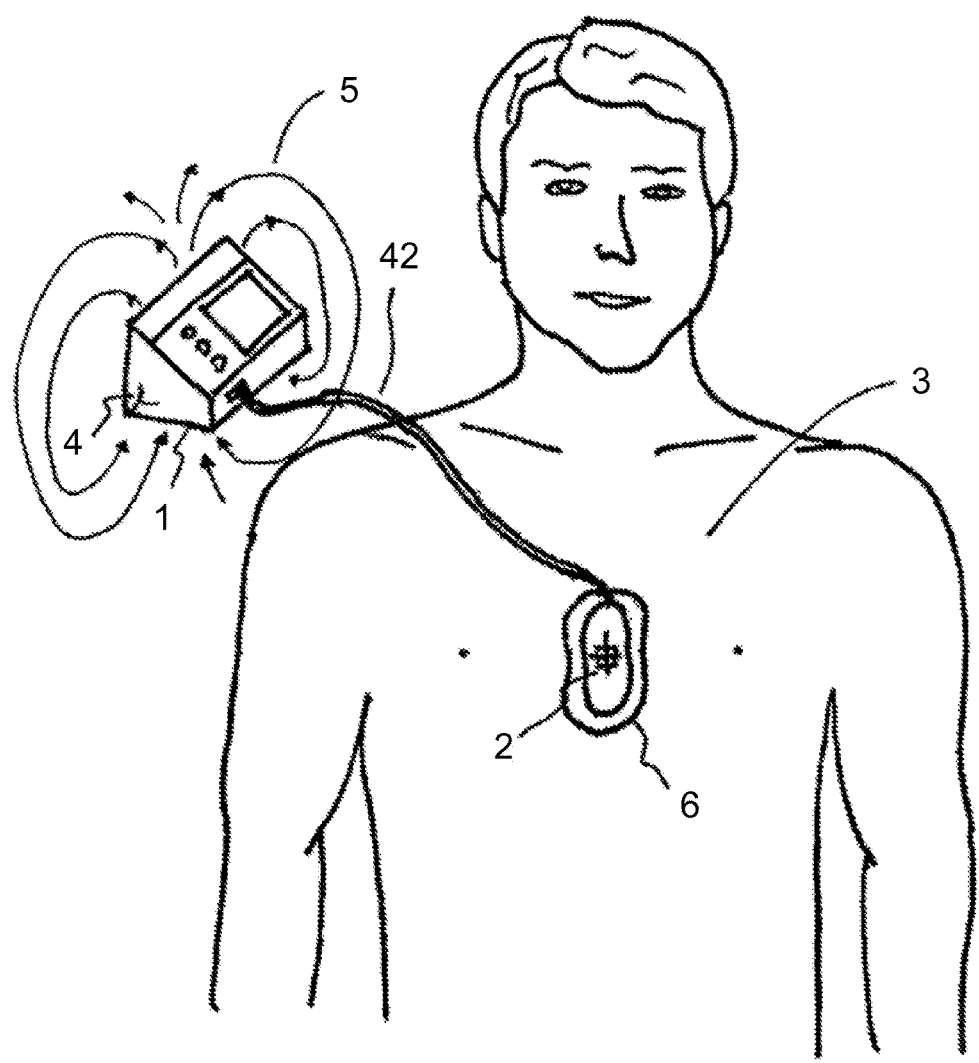
FIG. 2 is a top plan view showing a field detector of a CPR assist device within a pad on the patient's chest.

Reference is now made to FIGS. 1 and 2. In this example, the CPR assist device may include a relatively stationary base unit 1 containing a reference sensor 4 in the environment of an emergency and a position sensor 2 that may move according to a patient's chest movement, relative to the reference sensor 4, thus tracking the movement of the chest of the patient 3 during CPR. In this example, the reference sensor 4 is the field generator and the position sensor 2 is the field detector. The reference sensor 4 is capable of generating a signal, such as a field 5, that is detected by the position sensor 2. In this example, the position sensor 2 is provided in a structure placed on the chest of the patient, such as a block, pad 6 or other suitable structure. The CPR administrator or rescuer 9 may compress the chest of the patient directly by placing his or her hands 7 on the pad 6. Here, the base unit 1 is placed on the ground 10, which is relatively stationary relative to the patient. A cable 39 connecting the pad 6 to the base unit 1 provides power from a power source in the base unit 1 to the position sensor 2.

Figure 3:
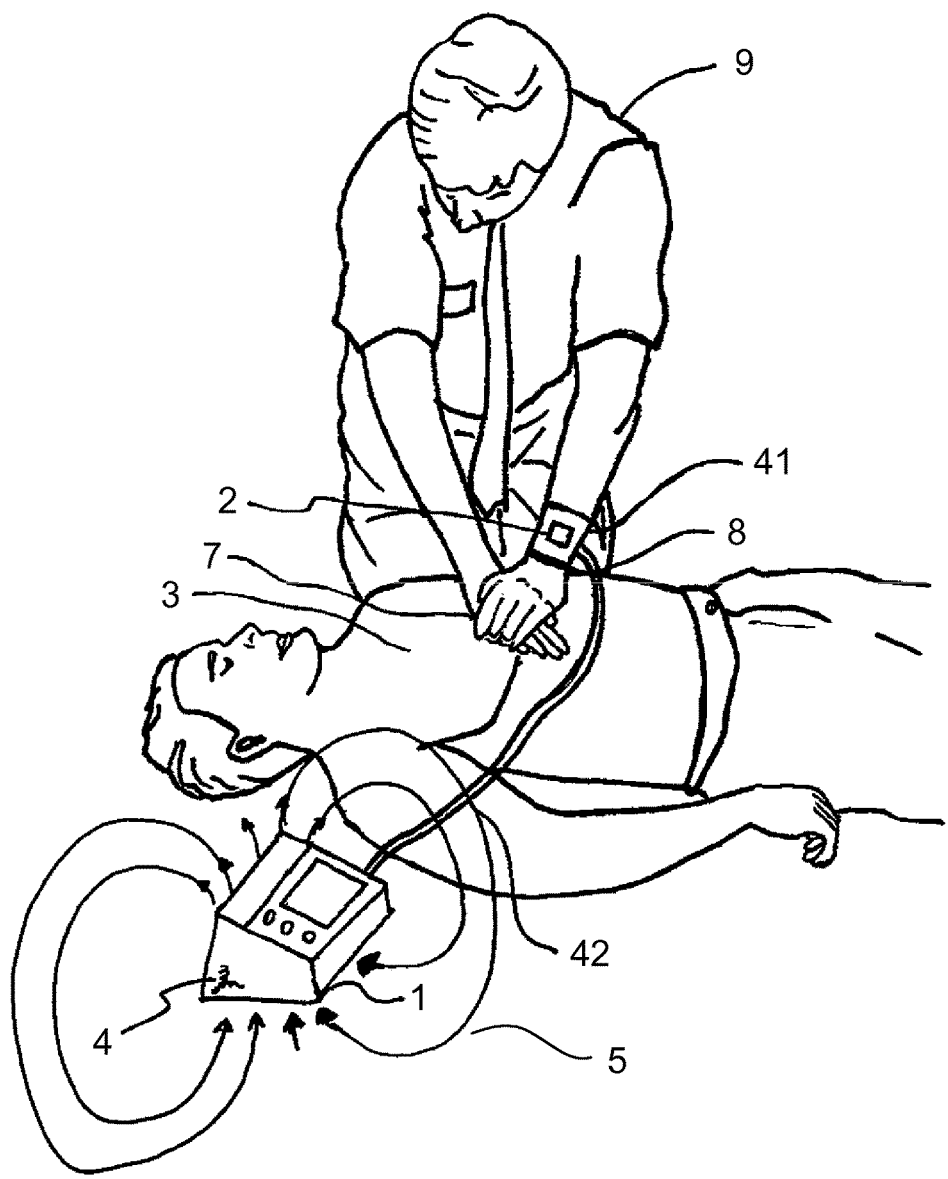
FIG. 3 is an illustration of a CPR assist device in accordance with an embodiment of the present disclosure.

Reference is now made to FIG. 3, showing another example of the CPR assist device. In this example, the position sensor 2 is located at the wrist 8 of the rescuer 9. For example, the position sensor 2 may be provided in a wrist band 38 that is worn by the rescuer. Although not shown, the position sensor 2 may alternatively be located at other positions on the rescuer, such as rescuer's hand 7 or arm, since movement of the rescuer's hand, wrist or arm typically corresponds with movement of the patient's chest during chest compressions.

Although not shown, the reference sensor 4 may be used without the base unit 1. The reference sensor 4 may be placed on an aspect of the patient's anatomy, such as the neck or forehead, which is relatively stationary. The reference sensor 4 may also be contained within another piece of relatively stationary medical equipment such as a defibrillator or medical monitor that is external to the patient.

The position sensor may be in contact with the patient's chest near the site of a chest compression or on the rescuer's hand so that the position sensor moves the entire distance of the chest during a compression. As the position sensor moves with the compression, its relative distance to the reference sensor also changes, allowing compression parameters such as compression depth, compression rate and compression angle to be determined.

Figure 4:
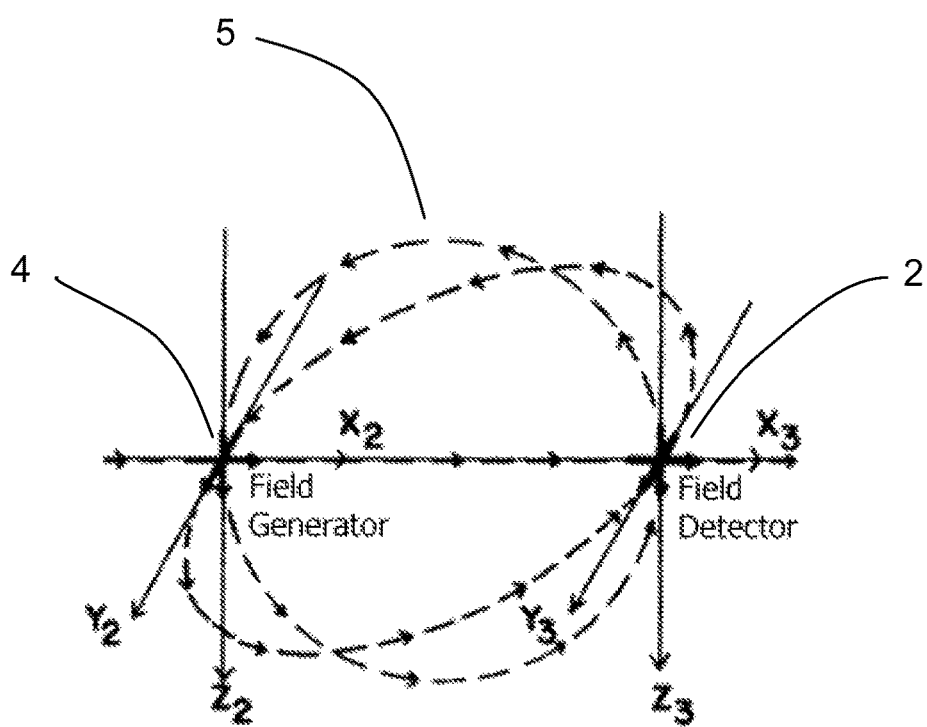
FIG. 4 is an illustration of a field generated by a field generator and detectable by a field detector suitable for an embodiment of the CPR assist device.

As shown in FIG. 4, the field detector (e.g., the position sensor in the above example) is configured to sense the generated field from the field generator (e.g., the reference sensor in the above example). The field detector may then produce a response signal. A processor determines the position of the position sensor, for example its three-dimensional position coordinates, relative to the reference sensor, based on the response signal. The processor may be provided together with the reference sensor in the base unit, may be provided on the position sensor, or may be a separate component. The processor may receive information from the position sensor through wired or wireless communication. The determination of the position sensor's coordinates may be accomplished by measuring the strength of the field detected from the field generator. More generally, where a signal is being transmitted between the reference and position sensors, the determination of the position sensor's coordinates may also be accomplished by measuring the response signal strength or the time-of-flight of the transmitted signal from the transmitter sensor to the receiver sensor. The processor may perform other calculations, for example calculations to determine the compression depth from the determined position information. The processor may also contain a memory for storing the position information, which may be useful for training or debriefing purposes.

As described previously, either the position sensor or the reference sensor may be used as the field detector, and the other of the pair may be used as the field generator. Multiple reference and/or position sensors may be used, which may further improve the accuracy of the position and orientation information. For example, in an environment with a significant source of noise or interference (e.g., in the case where the device uses electromagnetic fields as signals, one containing significant sources of metal), a second field detector may be placed in the environment of the first field detector, where the first field detector is used as a position sensor and the reference sensor is a field generator. This second field detector may be fixed in position and used to calibrate the measurements of the device by determining the ambient interference in the environment. In another example, a second field detector may be placed adjacent to the first field detector, both moving in accordance with the patient's chest, and the raw data from the two field detectors may be correlated to obtain more accurate position information. Additionally or alternatively, multiple field generators may be used to increase accuracy of the position information by having them placed in separate locations and correlating the signals sensed by the field detector. Also, multiple field generators may assist in eliminating ambiguity in positional data. For example, if one field generator and one field detector are used, each having orthogonal coils for electromagnetic signals, the coils of each of the field generator and field detector may align on their axes. If aligned, certain electromagnetic vectors will nullify and the amount of available useful data may be decreased. Using two field generators that are off-axis from each other may ensure that the coils of the field detector and are never aligned with the coils of at least one field generator. In this configuration, there will always be useful data available for determining position information regardless of the relative orientation of the field generators and field detector.

The position and/or orientation information determined from the sensors may be used to calculate CPR parameters such as the compression depth, compression rate, or compression angle, among others. Such parameters may determine the effectiveness of CPR. For example, a compression rate of 100 compressions per minute, a compression depth of 4-5 cm per compression, and a compression angle of about 90 degrees between the rescuer's forearm and the patient's chest has been found to be effective. In order to promote certain ranges for the parameters, feedback may be provided to the rescuer through feedback components on the CPR assist device. For example, there may be an audio cue, such as a beep, that sounds at the desired compression rate. The rescuer may also be provided feedback based on the calculated CPR parameters. For example, if the compression rate is lower than a pre-set desired rate, there may be an audio or visual cue to the rescuer to "compress faster". Similar audio and/or visual cues may instruct the rescuer in maintaining a desired compression depth or compression angle, among other parameters.

The CPR assist device may contain feedback components, such as embedded LED's, displays and/or speakers to provide audible and/or visual prompting and/or feedback. The prompts may consist of such statements as 'CALL 9-1-1' or 'COMPRESS FASTER' or 'COMPRESS HARDER' or 'GOOD COMPRESSIONS'. Images may also be displayed to guide the rescuer in proper technique. LED's or other lights may be used to pace the rescuer and provide visual feedback. A metronome may be used to audibly indicate proper compression rate to the rescuer. Such feedback components may be provided on the position sensor or the reference sensor, in the base unit if the base unit is used, or may be provided in a separate unit, such as a separate display unit.

The CPR assist device may be powered by a power source. A single power source may be used to power all components of the device, in which case one or more sensors may be connected to the power source by wires. Alternatively, each sensor may have its own power source, for example separate batteries provided with each sensor. The power source may be located in a separate base unit, which may also contain the processor. The sensor may then be connected to the base unit by wires.

Figure 5:
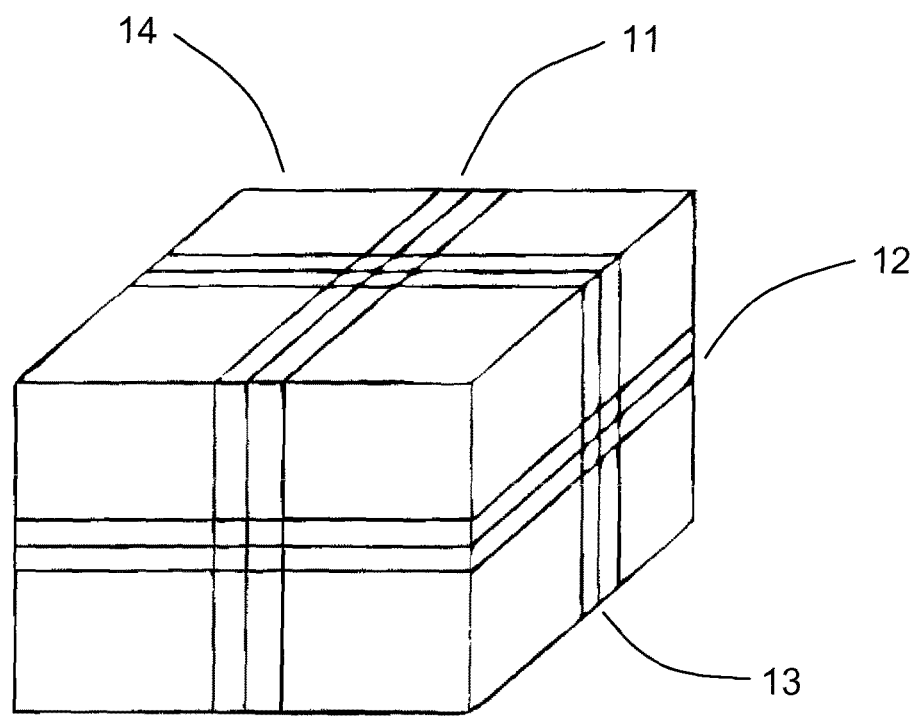
FIG. 5 is an illustration of a field generator or a field detector suitable for an embodiment of the CPR assist device.

Reference is now made to FIG. 5, which shows an example of a sensor. In this example, the sensor is a field generator or a field detector. The field generator and field detector in this example are electromagnetic coils or magnetic sensors.

Figure 6:
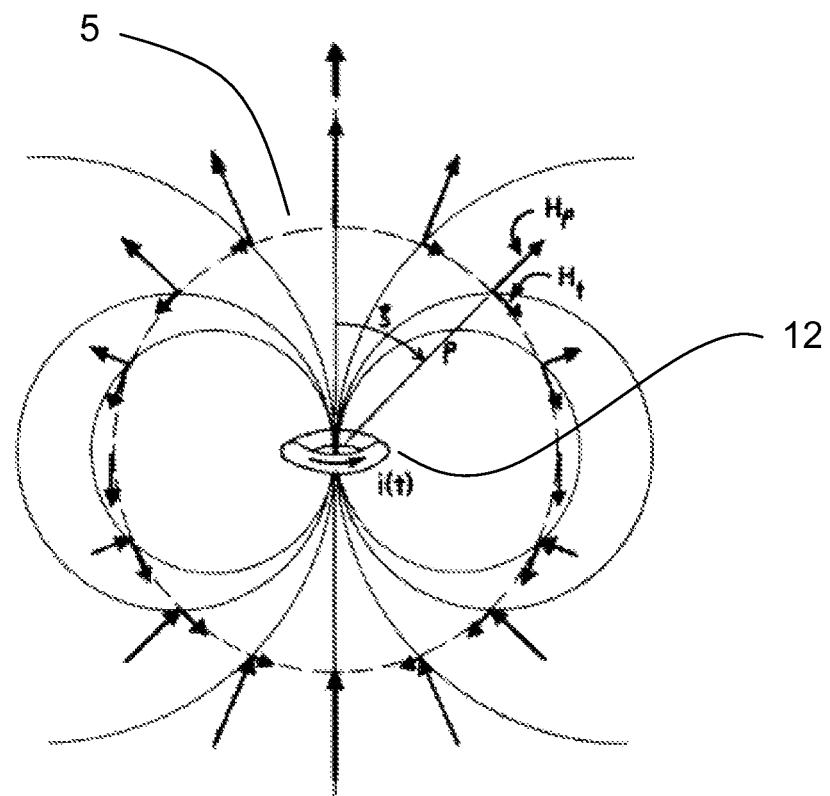
FIG. 6 is an illustration of a field produced by a coil in a field generator suitable for an embodiment of the CPR assist device.

The sensors may have a single coil on a single axis or multiple coils on multiple axes depending on the number of degrees of freedom desired in the position information. Here, there are three mutually orthogonal coils 11, 12, 13 wound around a solid core 14 composed of a suitable material, such as a plastic or a metal such as ferrite. If less degrees of freedom information is desired, there may be only two or only one coil used. FIG. 6 shows a field that may be generated by a one-axis coil contained within a sensor. Also, the field generator and/or field detector may contain more than three coils, and each may contain a different number of coils. For example, the field generator may contain nine coils and the field detector may contain one coil. By placing more coils in the field generator, fewer coils may need to be placed in the field detector thereby reducing the size, weight and thickness of the field detector. Using this approach, the field detector placed on the chest of the patient may be very small and thin, which may improve the patient's comfort and avoid any impedance to administering CPR.

Other designs for the sensors and coils may be suitable, as commonly known in the art. In an embodiment, the sensors each contain three mutually orthogonal coils. A signal, such as an electromagnetic field, is generated by each of the three coils in the field generator and detected by each of the three coils in the field detector, producing a response signal. The response signals may be used to compute the position of the position sensor relative to the fixed reference sensor in six degrees of freedom. Six vectors representing three translational axes and three rotational axes may be determined, allowing for measurement of compression depth and/or angle.

By providing position and orientation information in all six degrees of freedom, the sensor may provide full position tracking of the form of the rescuer's compressions. For example, where the position sensor is placed on the rescuer's wrist, six degrees of freedom information may provide rotation angles of the wrist, which may be useful in determining if the rescuer is administering CPR at an effective or desired angle to the patient's chest. With six degrees of freedom, a three-dimensional representation of the CPR administration may also be recreated later for debriefing, training, analyzing or other purposes. Although the sensors have been described as providing six degrees of freedom position and orientation information, the sensors may also be simplified to provide less information. For example, it may be suitable or sufficient for the sensors to provide two or three degrees of freedom information, such as where it is assumed that the compressions are largely in the z-axis (i.e., up and down) direction.

The field generator generates a field, such as electromagnetic energy where the sensors are electromagnetic coils, that is detected or sensed by the field detector. The strength of the electromagnetic signal detected on each axis of a multi-axis coil in the field detector allows the determination of position and orientation information. The generated electromagnetic field may be a pulsed DC field or an AC sinusoidal field. This generated field induces a voltage and current response signal in the field detector that is indicative of the distance between the coils in the field generator and those of the field detector.

The coils may be small for the generation of a small field over a short distance or larger if used for generating a larger field for operating over a longer distance. The design of the coils and the determination of the coil parameters may be particularly designed to suit the CPR assist device. Each coil may have precise geometry, with the same value of induction while being designed to be as small as possible. For example, the wire forming the field generator coil may be about 24-30 AWG copper wire making about 150-200 loops around the core. The size of the field generator that generates the field depends on the intended size of the radius of the field, but is generally larger in size than the field detector that detects the field. The field detector may be made relatively small, for example so that it may fit on the chest of a small patient, such as an infant. The field detector may be much smaller in size than the field generator. Due to the smaller area of the field detector coils, they may contain more turns of a smaller gauge of wire, for example 500-600 turns of 37 AWG, as compared to the field generator. The field detector may alternatively include other types of sensors, for example different magnetic sensors such as magnetoresistive sensors, Hall Effect sensors or fluxgate magnetometers.

Those skilled in the art will appreciate that, while an example of the CPR assist device uses coil-based sensors, this is not a requirement of the present method and device. Other sensors capable of detecting the position of an object, preferably in three-dimensional space, using a reference and position sensor may be used. For example, instead of coil-based sensors using electromagnetic fields, the sensors may use radiofrequency fields, acoustic fields, light fields, ultra-wideband fields, or radiofrequency identification fields, among others. The field used may be selected such that line-of-sight between the field generator and field detector is not necessary, so that the field is detectable through any obstacles between the two. This may allow the field generator and field detector to be conveniently placed, and may minimize the risk of not being able to detect the field, and hence CPR feedback information, during administration of CPR.

In some embodiments, it may be useful to add an accelerometer, tilt sensor or other orientation sensor to the reference sensor. This additional sensor enables the reference sensor to detect its own orientation or what plane it sits in. This may be particularly useful if the reference sensor is positioned on an incline. It may be useful to know the orientation of the reference sensor where the sensor are designed to provide less than six degrees of freedom position information, since the position and/or orientation of the position sensor is calculated relative to the reference sensor. Where all six degrees of freedom are sensed, knowing the orientation of the reference sensor may not be as important.

The reference sensor need not be at a fixed point on the ground beside the patient. The reference sensor may be located on any relatively stationary location near the patient, such as on a gurney, on a wall, on a ceiling, in a convenient location in a hospital room, inside an ambulance or any other appropriate location that is fixed and stationary relative to the patient, so that movement of the chest may be detectable. In particular, the reference sensor does not have to be absolutely stationary, it may be stationary only relative to the patient. For example, the reference sensor may be fixed in a moving ambulance carrying the patient, which would be acceptable since the reference sensor would still be stationary relative to the patient in the ambulance. Furthermore, the reference sensor may be affixed to a stationary portion of the patient or rescuer's anatomy. For example, the reference sensor may be placed on the forehead or neck of the patient. In another example, the reference sensor may be integrated into an electrode pad placed on the shoulder of the patient while the position sensor is positioned in a second electrode pad that conforms to the chest of the patient. The reference sensor may alternatively be worn or placed on the rescuer, at a relatively stationary point, for example the rescuer's legs, under the rescuer's knees (e.g., in a kneeling pad), around the waist of the rescuer, or any other suitable stationary aspect of the rescuer.

In an embodiment, the reference sensor may be incorporated or attached to another piece of medical instrumentation, such as a manual defibrillator or an automated external defibrillator (AED), that is relatively stationary. The position sensor may be affixed or placed in contact with the chest of the patient or the hand, wrist or arm of the rescuer. In an embodiment where the CPR assist device is used with a defibrillator or an AED, the position sensor may be positioned within one or both defibrillator electrode pads, the pad or pads being configured to extend into the chest region where the chest compressions are performed.

Figure 7:
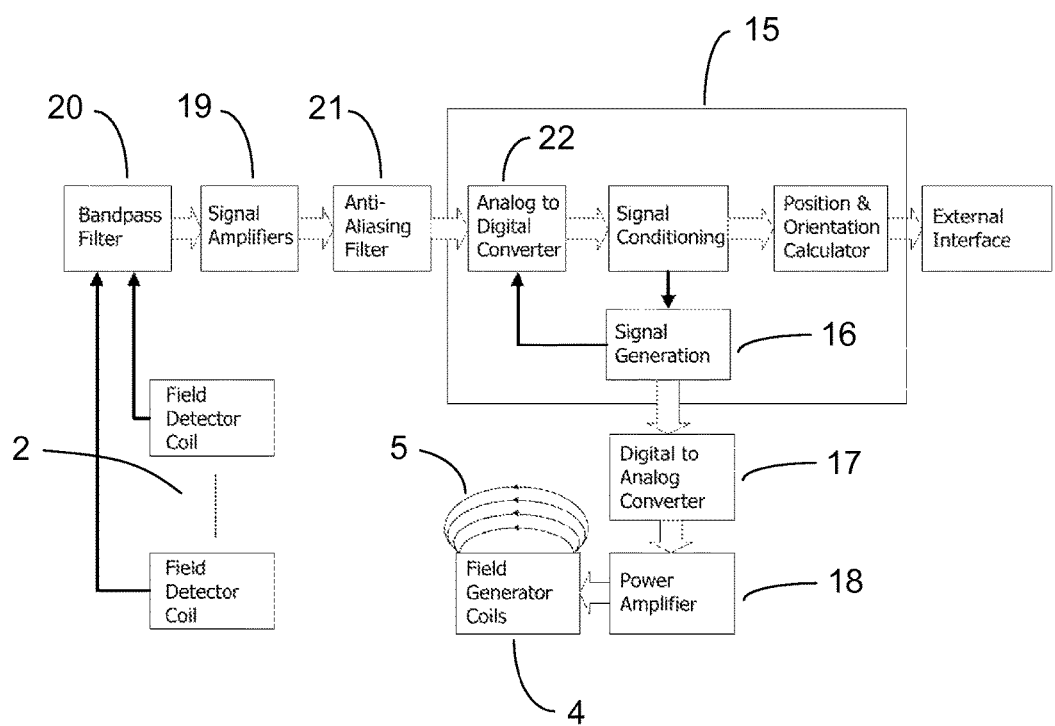
FIG. 7 is a block diagram illustrating a field generating and field detecting in an embodiment of a CPR assist device.

Reference is now made to FIG. 7, showing a block diagram of an example circuit for generation of the field and processing of the detected field. In this example, field generation and processing of the detected field are both performed by the same processor. Separate processors may also be used for each of field generation and detected field processing, in which case the block diagrams for the circuits would be separate, but may still contain similar blocks. For simplicity, the circuit will be described only for the example where a single processor is used, however a skilled person would know that the circuit may be modified to use two or more separate processors.

The circuit shown may be suitable where the generated field is an electromagnetic field and the sensors (e.g., field generator and field detector) contain coils for generating and detecting the field. In this embodiment, a field 5, such as a sinusoidal field, is generated by a waveform generator, such as a digital signal processor (DSP) 15, microcontroller or other suitable waveform generator. In the case of a DSP 15, the sinusoidal reference signal may be generated using a software look-up table 16. The sinusoidal wave signal is generated at a specific frequency, for example 12 kHz. A digital-to-analog converter (DAC) 17 is triggered at a certain sampling rate to transform the points in the software look-up table into a sinusoidal voltage. Alternatively, the sinusoidal signal may be generated by the DSP 15 by outputting a modulated pulse width modulation (PWM) wave using points from a look-up table. The PWM signal may then be low-pass filtered, for example using a second order RC filter (not shown). The low-pass filter produces a sine wave from the PWM signal, which is then fed to a power amplifier 18. The power amplifier 18 increases the strength of the sinusoidal signal before it is delivered to the coils for the generation of a time-varying field, for example the coils in the field generator. The power amplifier 18 may be a D-class, high power, low noise audio amplifier, or any other suitable amplifier as known in the art. In the case of a D-class amplifier, the output is PWM modulated, meaning that the sine wave is converted back into PWM format. Another low-pass filter (not shown), for example an LC lossless filter, may be used to produce a sine wave from the D-class power amplifier's PWM output. A multiplexer (not shown) may be used to select one of three coils contained within the field generator so that the field is generated for one of the three Cartesian axes. The amplified field is then detected by the field detector, for example where the field may be in the form of electromagnetic energy.

Figure 8:
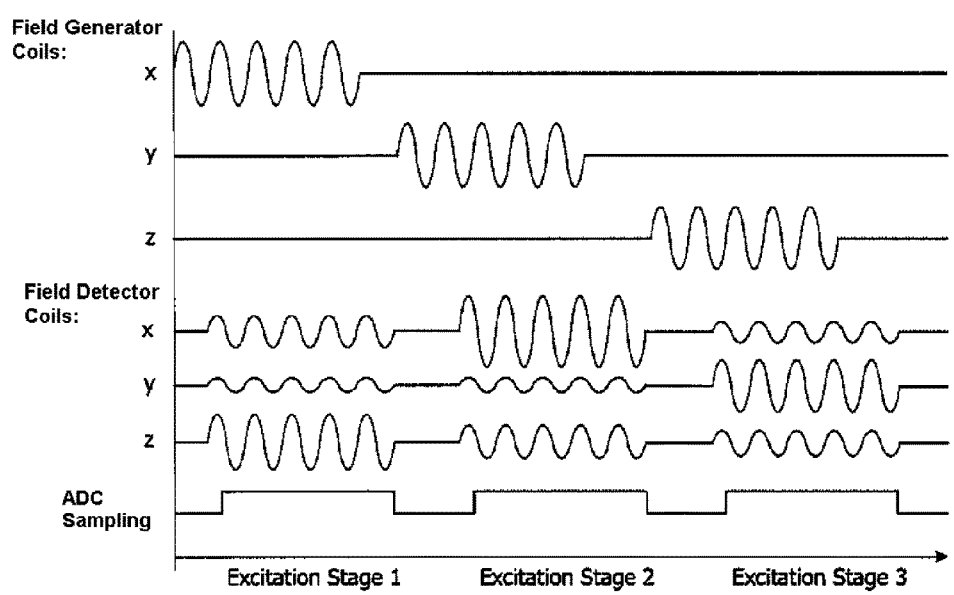
FIG. 8 is a diagram illustrating sinusoidal signals used to modulate a generated field from a field generator and sinusoidal signals detected by coils of a field detector in an embodiment of the CPR assist device.

FIG. 8 illustrates how the field 5 burst is sequentially delivered to each of the three coils in the field generator. This diagram represents an example in which there are three field generating and three field detecting coils. The three field generating coils, for example those in the reference sensor, are orthogonal to each other, as are the field detecting coils. Each field generating coil generates a sinusoidal field that is detected by the field detecting coils sequentially, in sequential excitation stages. Each excitation stage occurs for a duration of time during which excitation of the respective coil causes a field to be generated by that coil. The time duration of each excitation stage may be relatively short in order to avoid excessive lag, which may decrease the sampling rate. The reduction of lag by shortening excitation time may be balanced with the reduction of error by lengthening the excitation time. The time duration of each excitation stage may be variable, determined based on the specific embodiment, use or application of the device. As stated, the time duration may be balanced based on the desired error and the desired sampling rate. For example, in an application where error is the primary concern (e.g., in an environment prone to noise), the excitation stages may be longer. The field detecting coils are excited by the generated field depending on their orientation and distance relative to the respective field generating coil, producing a response signal. This response signal from the field detecting coils may then be sampled by an analog to digital converter to determine the field strength at each field detecting coil. During CPR, a relatively slow data rate may be acceptable. For example, if 40 position points are calculated per second, the actual time during which a sine wave is output from the power amplifiers would be less than $\frac{1}{10}$ of the total operating time. For example, it may be sufficient to output nine periods on each of the three field detectors to determine a position in space. Therefore, 27 total periods would be output per position. At 1.2 kHz, 27 periods occupy 2.25 ms. At 40 positions per second, the coils are active for 0.09 s or 9% of the total operating time thus ensuring that significant power is not being drawn by the system. If only two periods per detector are used, the total time that the coils are active would be 0.02 seconds or 2% of total operating time.

Although this example involves time-multiplexing the generated fields through each field generating coil, the fields may also be frequency multiplexed. If frequency multiplexed, the fields need not be sequentially excited, but may rather be excited at different frequencies. The field detector may then bandpass each of the detected fields to determine which of the field generating coils each originated from.

The generated field causes a response signal, for example due to an electrical potential that is induced in the coils of the field detector. The response signal may be sent to the processor and amplified, filtered and/or conditioned by the processor, as commonly done in the art. Amplification and filtering of the response signal from the field detector may be accomplished using a multi-stage approach in which multiple instrumentation amplifiers 19 are cascaded with filters such as bandpass 20, lowpass, differential and anti-aliasing filters 21. For example, a low noise, adjustable gain instrumentation amplifier may be used to receive the differential signal from the coils. The amplified signal may be bandpass filtered to remove noise outside the frequency of the specific sinusoidal modulating signal (e.g., 12 kHz). A second low noise adjustable instrumentation amplifier may be used to further amplify the filtered signal. Finally, anti-aliasing and low-pass filters may be used to remove any residual noise in the response signal. Other filters and/or amplifiers may be suitable, and may be used in an order different from that described here. The amplified and filtered signals are sent to analog to digital converters (ADC) 22 on the DSP for digitization and further processing. A high resolution ADC with a fast sampling rate may be used. The digitized signal may then be sent for signal conditioning.

The processor may determine the distance between the field generator and field detector by measuring the initial signal strength. If the initial signal strength is too low, the processor may alter the gain of the amplifier system. If the incoming signal is lower than what is necessary to provide adequate information (e.g. 8 bits of data), the gain may be increased. If the incoming signal strength is too low, the signal-to-noise ratio may be too high to obtain the desired information. As the signal strength is low, the gain should be increased. However, in some cases, as the system gain is increased, the noise level is also increased and the difference between signal and noise may become too small to measure accurate data. For example, if using a high speed, programmable gain instrumentation amplifier such as the AD8253 from Analog Devices, the gain may be changed from unity to a gain factor of up to 1000. Two pins on the instrumentation amplifier set the gain depending on if they are high or low. For example, if both pins are low (i.e. 0,0), the gain is the minimum value of 1. If the pins are (1,1), the gain is the maximum value of 1000. Other combinations result in gains of either 10 or 100. Therefore, the gain may be controlled by software in the DSP that appropriately toggles the gain setting pins on the amplifier. The gain factor may first be increased from unity to 10. If the newly amplified signal remains too low, the gain may be once again shifted higher to a factor of 100 by altering the high-low state of the gain setting pins on the amplifier. This process may be repeated until the signal level is sufficient or the gain factor is at its maximum level. Furthermore, the device may be able to detect when the field detector is outside of a given operating radius. When the response signal is less than the desired number of bits of data (e.g. 8 bits) and the amplifier is already at the maximum gain (e.g. 1000), the device may determine that the field detector is beyond the operating range of the device and this may be indicated to the user, for example through a visual display or an audio signal. Since the operating range of a field detector that is tethered to the field generator (e.g., by a power cable) may be limited by the length of a cable, this may not be a particularly important issue for such a device.

Dynamic gain may also be implemented by varying the current through the coils of the field generator. At close range, the current through the field generating coils may be reduced instead of and/or along with a decrease in amplifier gain. Adjusting the current through the field generating coils serves at least two purposes. First, in combination with an adjustable gain amplifier, the adjustable current may provide a greater dynamic range of signal strengths and hence may allow a greater operating range for the device. Secondly, adjustable current may allow the device to conserve power at close distances and increase power when operating at the outer limits of its operating range. This may help to conserve power which may be particularly important when the device is operating on battery power, for example when the device is designed to be portable.

Figure 9:
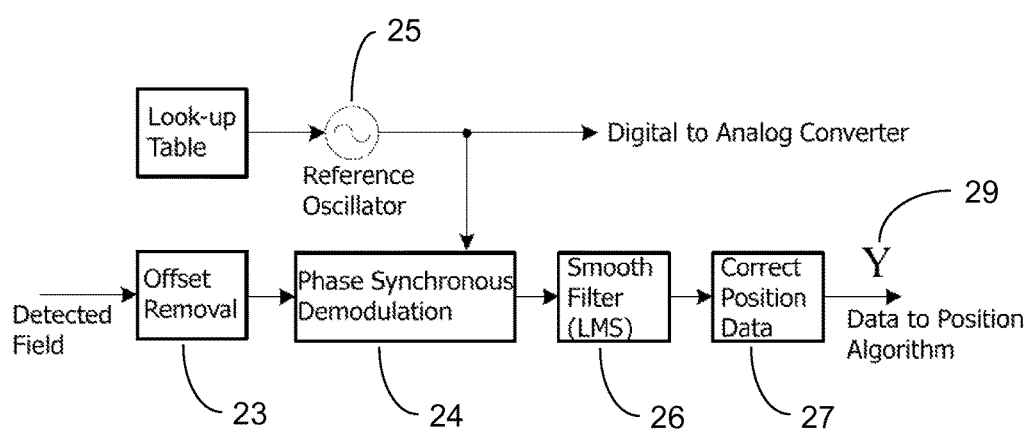
FIG. 9 is a block diagram illustrating a signal conditioning process within the digital signal processor in an embodiment of the CPR assist device.

After digitization, the signal may undergo further conditioning and/or filtering as shown in FIG. 9. An offset removal algorithm 23 may be applied to the signal once it is received from the ADC 22. This algorithm removes any DC offset component which may be present on the response signal and which may disrupt correct operation of the demodulator. In this algorithm, a running average of the input signal is maintained and subtracted from each input reading. The average value of a true sinusoidal signal is zero and over a complete number of cycles, only the DC offset component remains. This offset may be subtracted from the analog-to-digital converted signal on a point-by-point basis.

A second stage of conditioning may comprise a demodulator 24 synchronized to a reference oscillator 25 to determine the phase shift of the response signal and yield a full-wave rectified sinusoidal wave of the appropriate polarity. The use of a digital technique to produce the reference oscillator may allow the reference signal to be readily available, permitting a simple demodulation technique to be used which is insensitive to phase shift. The response signal may be thought of as a complex vector, the real and imaginary parts of which may be computed independently by multiplying with the two quadrature components. The magnitude of the vector may be computed from the root of the sum of the squares of these components. The determination of phase is based on the result of an 'exclusive OR' between the sign of the reference oscillator and that of the response signal: if these signals are in phase the signs should be the same and the result is false. If the signals are in anti-phase the signs are opposed and the result will be true. Phase may be determined using a 'majority vote' based on the previous results over one complete oscillator cycle. The phase of the detected signal may be indicative of what quadrant in space the sensor is operating within.

A third stage of signal conditioning may be a smoothing filter 26 used to smooth the rectified signal magnitude into a stable digital result. The smoothing may be used to remove ambient noise, such as the presence of magnetic field distortion in the air surrounding the system. A simple moving average filter may be constructed using a window over the whole excitation step. Such a filter runs on a point-by-point basis: each data point from the output of the demodulator is added to a circular buffer, and the average may be computed by subtracting the oldest value from a running total, adding the newest value, and scaling. This smoothing may also be done by demodulating the signal using the reference signal from the reference oscillator 25 in addition to the smoothing filter 26 described above. The reference signal for signal conditioning may also be provided by the position sensor, as will be described below. The DC-offset removal, demodulation and smoothing may be performed by the processor on the response signal in real-time as the data is made available by the analog-to-digital converter. Alternatively, these operations may be performed once all nine values from each field generator-detector combination are received.

A fourth stage of signal conditioning may provide sensor geometry correction 27 to correct raw position data. Fixed offset and gain adjustments may be applied and the result may be used to index into a correction map to retrieve a correction in bits which is added to the reading. The correction map may be created in a calibration step, which may be particularly suitable where the device is used in a relatively fixed, constant or controlled environment. For example, in a fixed environment, such as a training centre or a home, the surroundings may be mapped prior to any use of the device in order to account for sources of signal noise, such as metal objects. This calibration may be useful for researchers using the device for CPR research in a controlled setting. Common calibration methods may be used to create the correction map, and such calibration may be accurate well into the sub-millimeter range. In an emergency environment where there is less setup time, the calibration step may be less suitable. Furthermore, calibration information related to the specific coils being used (e.g., inductance, size, shape, gain) may be stored with the coil on an EEPROM or other such memory device for retrieval by the processor. The processor may then apply this coil-specific calibration information to the position calculations. Other signal conditioning algorithms may also be used instead of or in addition to those described above, as commonly known in the art.

After appropriate filtering and conditioning, a matrix Y 29 representing the induced voltages in the coils of the position sensor may be composed, as shown in FIG. 10. In this example, the matrix Y 29 contains nine measured voltages 28 and their signs as obtained from the coils of the position sensor. From the matrix Y 29, the position and orientation may be estimated using commonly known algorithms.

The position and orientation information may be determined using various mathematical techniques, as commonly known in the art. One algorithm that may be used is described below, although any other suitable algorithm may be used. This algorithm may be suitable where the position information is determined for six degrees of freedom. The algorithm may be changed and/or simplified for less degrees of freedom.

Figure 11:
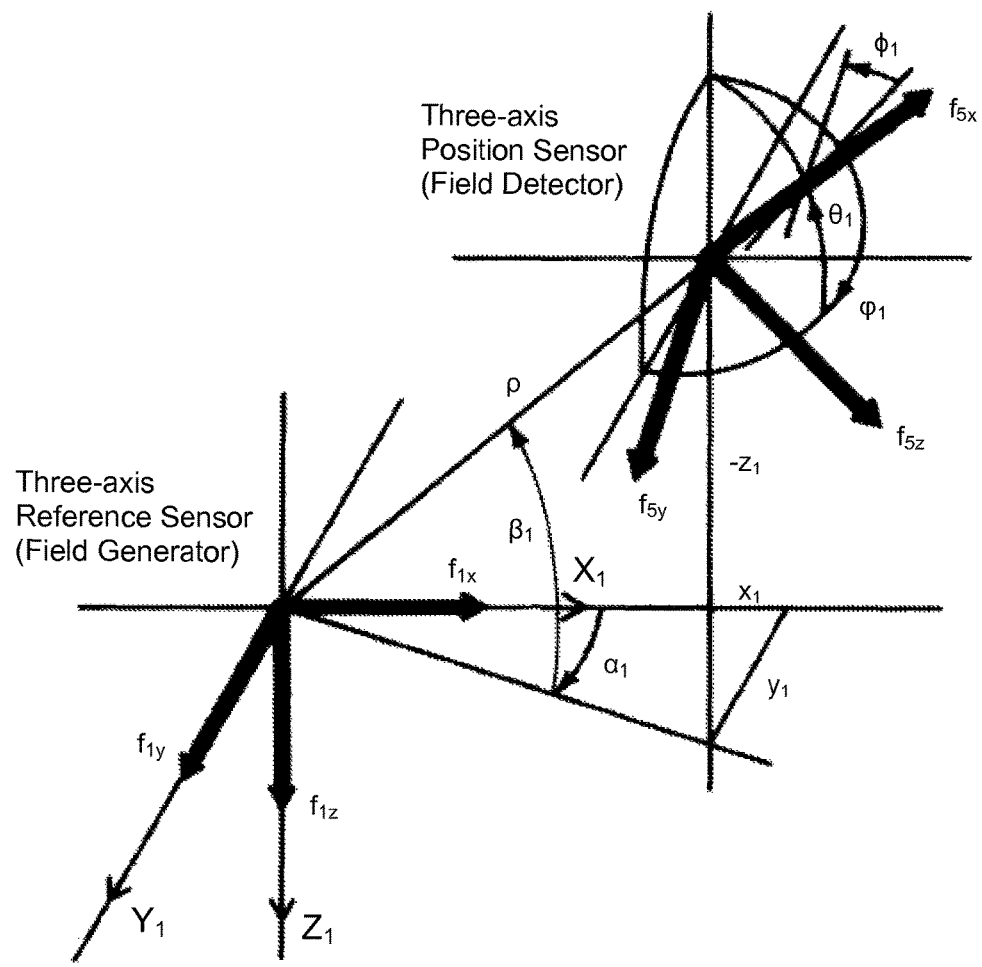
FIG. 11 is an illustration of a three-axis field generator and detector suitable for an embodiment of the CPR assist device, and the corresponding electromagnetic vectors.

The near magnetic field produced by circular loop antennas, such as coils in the position sensor, may be described in terms of radial and tangential components as shown in FIG. 11. A loop is excited with a current $i(t)=I \cos \omega t$, where I is amplitude of the current, $\omega$ is phase and t is time. The magnetic field produced at a point of distance $\rho$ and off axis angle $\delta$ is described completely by radial and tangential components:

$$H_p=(M/2\pi\rho^3) \cos \delta \text{ and } H_t=(M/4\pi\rho^3) \sin \delta$$

where M=NIA is the scaled magnetic moment of the loop and A and N represent the area and number of turns of the loop, respectively. The sensor loop antenna responds only to the field component aligned with the loop orientation vector (i.e., perpendicular to the plane of the loop). Measurements of three orthogonal generated fields from ground antennas as detected by the set of three orthogonal field detecting antennas produce information which is sufficient to determine six position and orientation parameters. This assumes orientation and position parameters are independently determined. To synthesize a position-orientation algorithm, coordinates and a vector-matrix formulation relating sensor output to source excitation must be defined using the geometric relationship between a three-axis source and a three-axis sensor.

Figure 12:
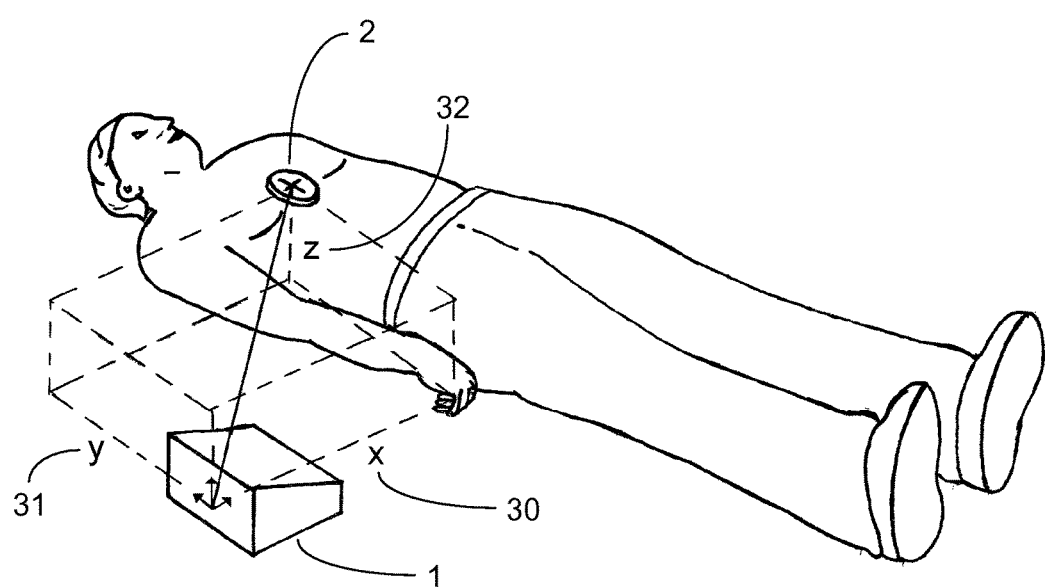
FIG. 12 is a diagram showing the distance between a base unit and a position sensor, as represented by the three coordinate axes, in accordance with an embodiment of the present disclosure.

Position may be calculated independent of sensor orientation resulting in three degrees of positional information as shown in FIG. 12. Alternatively, all six degrees of freedom (position and rotation) may be obtained. In the case of CPR, it may be adequate to use three degrees of freedom, primarily the x 30, y 31 and z 32 coordinates, to measure compression depth. To calculate the x, y and z values, various approaches may be taken. A suitable algorithm involves the calculation of vector magnitudes and dot products from the nine induced voltages. Various matrix operations may be used to determine x, y and z positions as well as all three orientation angles, as would be well understood by a person skilled in the art.

From the geometrical relationship and the aforementioned equations, an estimation algorithm may be implemented comprising the following steps:

1. Measure the coupling between field generator and field detector to obtain a matrix Y 29 and filter it.
2. Compute the orientation invariant matrix $D=1/C^2 Y^T Y$, where C is a gain constant based on the known amplification of the signal.
3. Estimate the positions x, y and z from $D^2$.
4. Compute $D^{-1}=(D^2)^{1/2}$.
5. Estimate the orientation matrix $A=1/CYD^{-1}T_c$ where $T_c$ is the compensation rotation matrix.
6. Estimate the orientation angles $\psi$, $\theta$, $\Phi$ from the matrix A.

All six position and orientation coordinates are available at the output of this algorithm. Other estimation algorithms may be used, as commonly known in the art.

From the calculated position and orientation information, CPR parameters may be calculated. For example, compression depth, compression rate and compression angle may be calculated based on the position and orientation information, as would be known by a person skilled in the art. Some example algorithms will be described, but a person skilled in the art would understand that other algorithms may also be suitable. In the case of compression depth, the x 30, y 31, and z 32 positions may be used to determine the distance traveled on the axis of the compression. The compression depth may also be calculated by assuming that all motion of the coil is motion due to the chest compression. This assumption may be particularly valid in certain embodiments, such as a pad affixed to the chest of the victim where the pad moves only with the compression. With this assumption in place, the compression depth may be measured by calculating the change in the magnitude of the position vector at each point in time. The magnitude of the position vector at any point in time is equivalent to the square root of the sum of squares of the x, y and z positions. Rotational angles may be used to further define the trajectory and angle of the compression. Rotational angles may be particularly important in certain embodiments such as a glove where the angle between the rescuer's forearm and the victim's chest may be important for accurate compression depth estimation.

Parameters such compression rate may be calculated by using peak detection algorithms capable of determining the occurrence of a true compression event. Peaks may also be detected by setting specific threshold values that a compression must achieve in order to be considered a true compression. For example, if a compression passes 3 cm in depth and recoils to 2 cm in depth, it may be considered an adequate compression. Counting compressions not only enables the calculation of compression depth but also enables a compression countdown in which each of the 30 compressions comprising one cycle of CPR are counted down. Such information may be provided to the user so that he or she does not have to keep track of or count the number of compressions during the CPR process.

These calculated parameters may be provided to the rescuer as visual, audio and/or tactile feedback. The calculated parameters may be compared against pre-set target ranges and feedback may be provided accordingly. This information may also be stored in the processor for later analysis, such as for training purposes.

There are certain characteristics of a chest compression that may allow the depth measurement system to be further refined. A chest compression is a relatively short and consistent cyclical movement. The entire downward stroke of a chest compression is usually between 2 cm and 6 cm and is a translational movement occurring primarily on the z-axis (i.e., up and down). Chest compression analysis typically does not require complex motion analysis accounting for a wide range of movements covering a large area. Chest compressions are typically simpler and the characteristics of a compression may be used to simplify the device's architecture and size, reduce the device's power consumption, reduce the device's cost and/or enhance the device's accuracy.

Figure 13:
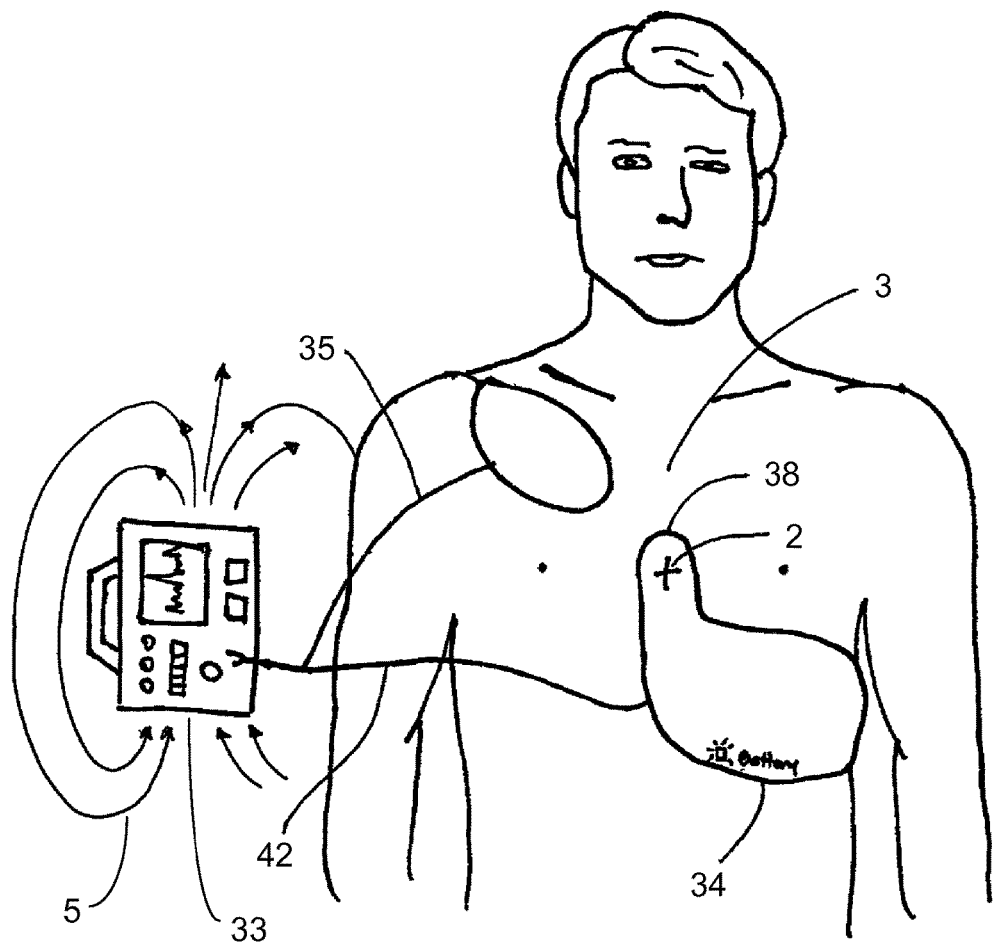
FIG. 13 is a top plan view showing a field generator embedded inside a defibrillator and a field detector embedded inside a defibrillator pad, in accordance with an embodiment of the present disclosure.

For example, the distance between the field generator and field detector may be minimal thereby decreasing the power requirements of the device. In an embodiment shown in FIG. 13, the reference sensor is provided in a defibrillator unit 33 present at the scene of the emergency. The position sensor 2 is provided in one of the defibrillator's electrode pad 34 (e.g., in an extended portion 38 of the pad 34) or some other structure placed on the patient's chest or the rescuer's hands, wrist or arm. The typical distance between a defibrillator and the chest of the patient is short, typically ranging anywhere from about 0.3 m to about 1.1 m. Typically, defibrillator electrode pads have cables 35 connecting them to the defibrillator unit 33. These cables are typically between 0.8 m and 1.1 m in length and, therefore, the defibrillator unit 33 is typically placed less than one meter away from the patient. Consequently, the field generator typically needs to generate a field extending no more than about one meter in radius that is detectable by the field detector. Since electromagnetic energy decreases in strength in cubic proportion to the separation between the generator and the detector, this short generation distance means that the power requirements of the field generator are lessened, where the generated field is an electromagnetic field.

Furthermore, device architecture may be simplified by limiting the operating range of the device. Over a short distance, a fixed gain amplification rather than a dynamic gain amplification may be sufficient to amplify the response signals. Fixed gain amplification may allow for the integration of simpler device components at a lesser cost. Reduced field size may also allow for an increase in accuracy by reducing the possibility of noise. A small field size may allow the gain of the amplifiers to be accurately fixed so as to optimize performance over the operating range. There may be other design considerations aside from obtaining the maximum field size. For example, the minimum field size may be important. To reduce the need for a wide dynamic gain range, the minimum radius of field generation may be limited to prevent saturation of the response signal when the field generator and field detector are very close together. This may be accomplished, for example, by placing the coils of the field generator away from the outer sides of the field generator's enclosure or by locating the field generator away from the outer sides of the base unit (e.g., where the field generator is provided in a base unit), so that the coils of the field generator cannot be physically adjacent to those of the field detector. Filtering, signal conditioning and signal amplification may be tailored to function effectively over the short distance in which the chest compression takes place.

Figure 14:
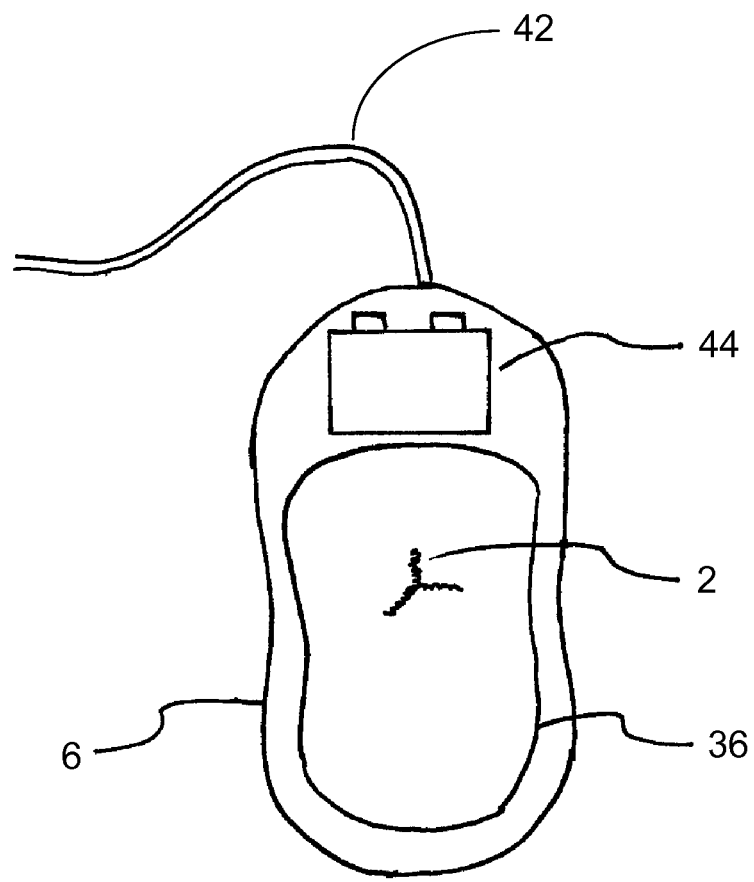
FIG. 14 is an illustration showing a pressure sensor adjacent to the field detector inside an embodiment of the CPR assist device to be placed on the chest of the patient.

A pressure switch or pressure sensor 36 may also be included with the CPR assist device to further improve accuracy as shown in FIG. 14. In this example, the pressure sensor 36 contains the position sensor 2, and both are provided on a pad 6 that may be placed on the patient's chest. The pad 6 also contains a power source 44 for the position sensor 2. The pressure sensor 36 or switch may be provided with the position sensor 2 and may act as an indicator for indicating to the device when a compression has commenced. For example, the pressure sensor 36 may be located between the hands of the rescuer and the patient's chest, so that the pressure sensor 36 may detect the start of a chest compression as a sharp increase in pressure. The processor in the device may then begin measuring the relative distance that the position sensor 2 has moved through the compression once the start of a compression has been indicated. Similarly, the end of a chest compression may be detected by the pressure sensor 36 as a release of pressure. By measuring the relative distance between the initiation and termination of a single chest compression, the magnitude of possible errors may be reduced. Measuring the relative positional change may be more effective and accurate than constantly calculating the more error-prone absolute distance between the reference and position sensors. Because the pressure sensor 36 may be used to detect the start and end of a compression, the pressure and/or force signal from the pressure sensor 36 may additionally be used to provide information on the duration of a compression, the velocity of a compression or the frequency of compressions.

The pressure sensor or switch may also be used to determine the force exerted during a chest compression and correlate it to the position information calculated from the field detector's response signal. The force signal from the pressure sensor may be indicative of the nature of the compression (e.g., the duration of a compression) and may be useful in filtering the response signal. For embodiments where an electromagnetic field is being generated and detected, the force and/or pressure signal may be useful for reducing error due to metallic objects in the environment since force is not affected by the same sources of error as detection of such a field. The force exerted during CPR may not be useful for directly computing compression depth since victim body type, chest compliance and other variables affect the amount of pressure required to attain a certain compression depth. However, the force and pressure signal provides a waveform which may be used as the reference signal for processing the response signal as described above with respect to FIG. 9, for example by providing an indication of the start and end of a compression. By using the force signal as a reference for the response signal, together they may provide more accurate chest compression position information.

Figure 15:
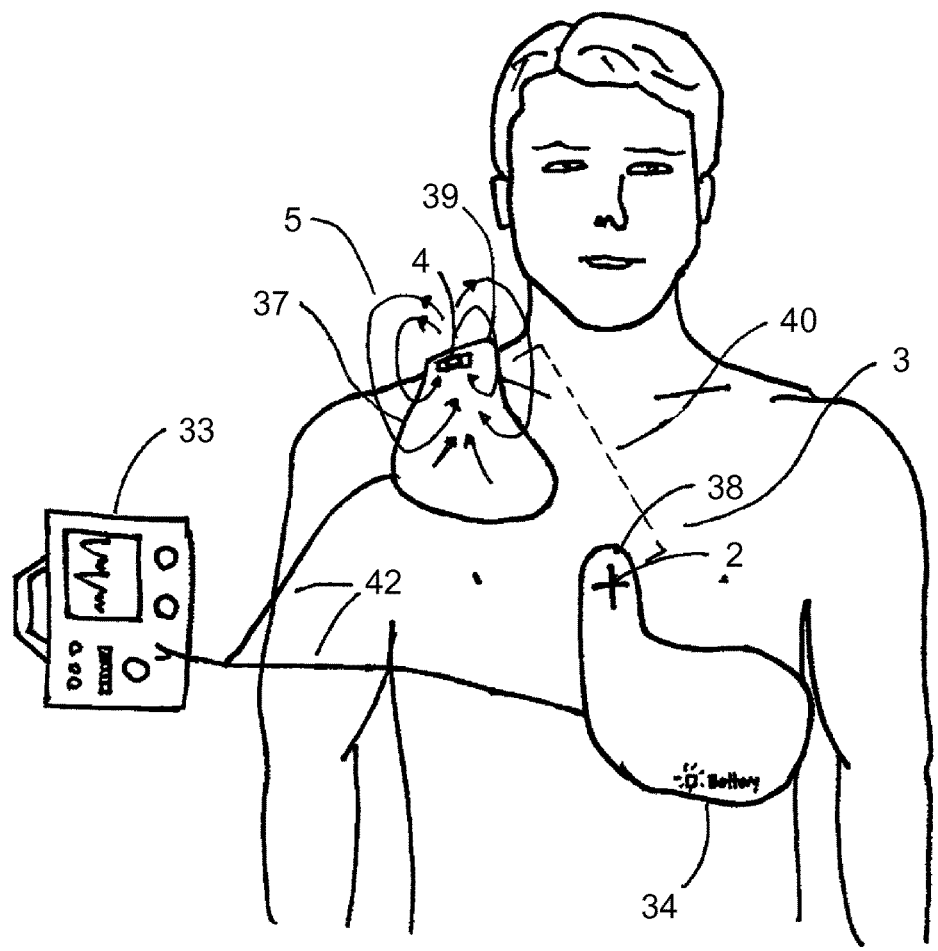
FIG. 15 is top view showing an embodiment of the CPR assist device in which the field generator is integrated into a stationary portion of the upper defibrillator electrode pad and the field detector is embedded into the lower electrode pad.

In another example shown in FIG. 15, the reference sensor 4 and the position sensor 2 may be incorporated into a single unit or may be both placed on the anatomy of the patient. For example, during the defibrillation process, two electrode pads 34, 37 are typically applied to the chest of the patient in two specific locations. One pad 37 may be positioned just below the right shoulder of the patient while the other pad 34 may be placed on the lower left side of the patient. These electrode pads may be extended so that one of the pads extends into the center of the chest where the CPR is performed. Within the extended portion 38 of the pad, the position sensor 2 may be embedded so that it sits below the rescuer's hands during administration of CPR. The reference sensor 2 may be placed in the opposing pad 37. The electrode pads 34, 37 may be designed in such a way that the pad 34 containing the reference sensor 4 has a portion 39 that does not move when a chest compression is administered. The reference sensor 4 would then remain stationary relative to the patient and may be affixed to a stationary component of the patient's anatomy. By locating both the reference and position sensors 4, 2 on the body of the patient, the size of the generated field may be reduced. Typically, reducing the field size reduces device complexity, power requirements, as well as device size, as described above. In addition, if both the reference and position sensors 4, 2 are placed in a fixed or approximately fixed location relative to each other, the measurements performed by the device may be made more accurate. Firstly, by knowing the approximate relative starting distance 40 between the sensors, an appropriate amplification gain for the response signal may be selected that allows the entire duration of a chest compression to be properly amplified. A known field size and a short overall movement during a compression of 6 cm or less may allow the device to operate with a simple fixed gain rather than a more expensive and complex dynamic gain. Secondly, by having the sensors nearby and on the patient's body, external sources of noise may be, more easily eliminated and/or compensated for.

The major sources of noise, primarily large metallic objects for electromagnetic fields, may mostly be absent in the vicinity of the patient's chest. Two characteristics of a metal determine the extent to which it will distort an electromagnetic field. The first property is the conductivity of the metal. AC sinusoidal electromagnetic fields generate eddy currents in conductive materials. The extent to which eddy currents are produced is dependent on the size and conductivity of the material. Very conductive metals, such as copper, are more threatening to the field than less conductive metals such as steel. The second property is the permeability of the metal. Materials that are highly permeable at the frequency of the generated field (e.g., 12 kHz) may skew the detected field. The major sources of noise in a CPR environment are such items as rings, watches and piercings worn by the patient or rescuer, which are typically too small to significantly disrupt the field. Other sources of noise, such as the conductive material of the defibrillator pads or implants in the patient, are also unlikely to result in significant interference. Defibrillator electrode pads and implants typically use metals with low conductivities that are resistant to corrosion, such as tin and titanium respectively. By keeping the field generator and field detector close together on the body of the patient, these metallic sources of noise may be reduced as the effect of noise from these metal sources grows exponentially with the distance between the field generator and field detector. Furthermore, by having the sensors placed in a known configuration, the starting distance between the two sensors may be approximated. This approximation may be used to calibrate the device before it begins calculating compression depth. Calibration methods may compensate for error by comparing the approximate known distance between the sensors with the measured distance. The calculated error may be used to determine the approximate effect of metallic distortion in the environment.

Figure 16:
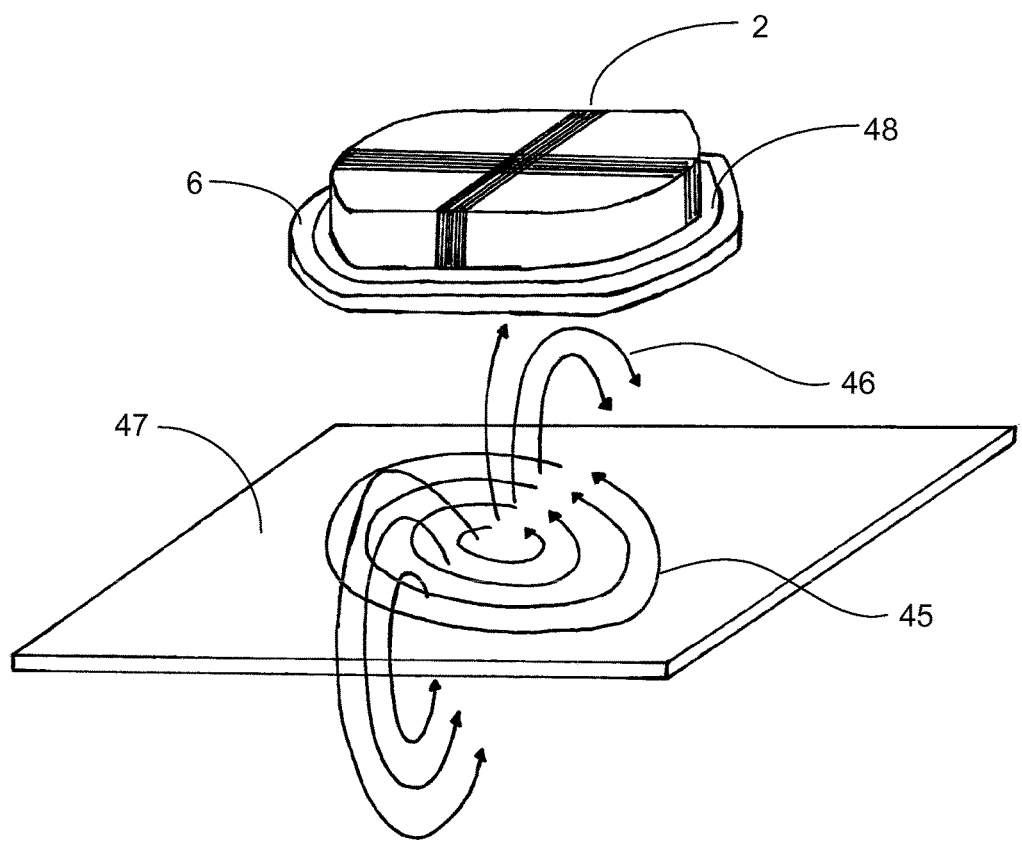
FIG. 16 is an illustration showing a position sensor with a metal foil underside suitable for an embodiment of the CPR assist device in accordance with an embodiment of the present disclosure.

In the case of CPR, the primary sources of metallic interference are typically those under the patient such as a metallic gurney or metal floor. To subdue the effect of eddy current 45 induced secondary magnetic fields 46 emanating from the metallic surface 47 beneath the patient, a conductive foil 48 or sheet may be placed directly under either the field detector coil or field generator coil or both coils, for example as shown in the embodiment illustrated in FIG. 16. In this embodiment, the metallic foil or plate may be the size of the coil and may be placed attached to the coil. In the case of the field detector being a pad placed on the chest of the victim, the metal foil may be attached to the bottom surface of the pad so as to deflect or absorb fields generated by the metal surface below the patient. The properties of the foil placed beneath the coil would be known to the device and the processor would thus be able to compensate for its addition to the device. Essentially, the effects of a large metal surface below the patient may thus be mitigated through the use of a known conductive layer between the coil and the metal surface.

Other methods of overcoming distortion and interference are possible. For example, Kalman filters may be used to recursively estimate the dynamic motion of the position sensor. These algorithms use previous states and error of the system to estimate future movement. Also, Bernstein polynomial techniques have proven to be effective in interpolating distance in the presence of serious noise and interference. Other correction methods may be suitable, and would be known to those skilled in the art.

Large variations in temperature may alter the properties of the coils resulting in some level of error. Therefore, temperature sensors may be placed within or adjacent to the field generating and field detecting coils to provide thermal correction coefficients based on the ambient temperature. The addition of the temperature sensors to the device may eliminate signal drift associated with temperature fluctuations.

In some embodiments, the reference or position sensor may be positioned on, around or about the rescuer's hand or wrist. The sensors may be embedded inside a glove, a wrist band 41 (FIG. 3), a wrist support device or similar articles. In an example where the position sensor is worn on the rescuer's hand or wrist, the position sensor may move with the hand of the rescuer as the hand of the rescuer moves with the chest compression. Therefore, position information of the rescuer's hand may be translated into position information of the patient's chest. The position of the patient's chest may be thus used to determine compression depth and other parameters. Furthermore, the device may be configured to detect six degrees of freedom of position information. Therefore, rotation angles may also be calculated. A sensor worn or located on the wrist of the rescuer may be used to calculate chest compression angle, which is the angle of the rescuer's arm relative to the chest of the patient, using this rotation information. This angle may be important as a perpendicular angle typically results in the maximum transfer of force and better administration of CPR. Ensuring that the rescuer is performing CPR with proper technique and angle may help to reduce rescuer fatigue, discomfort and injury. The rotation angle of the rescuer's wrist may be easily calculated using the mathematical methods described above.

As previously stated, in some embodiments, the position sensor may be the field generator (or more generally the transmitter sensor) and the reference sensor may be the field detector (or more generally the receiver sensor). For example, the position sensor may be placed in a pad on the chest and may generate a field that is detected by the reference sensor in a defibrillator next to the patient. In some embodiments, the sensor on the patient or rescuer is tethered by a cable 42 (FIG. 1) to the reference sensor.

Figure 17:
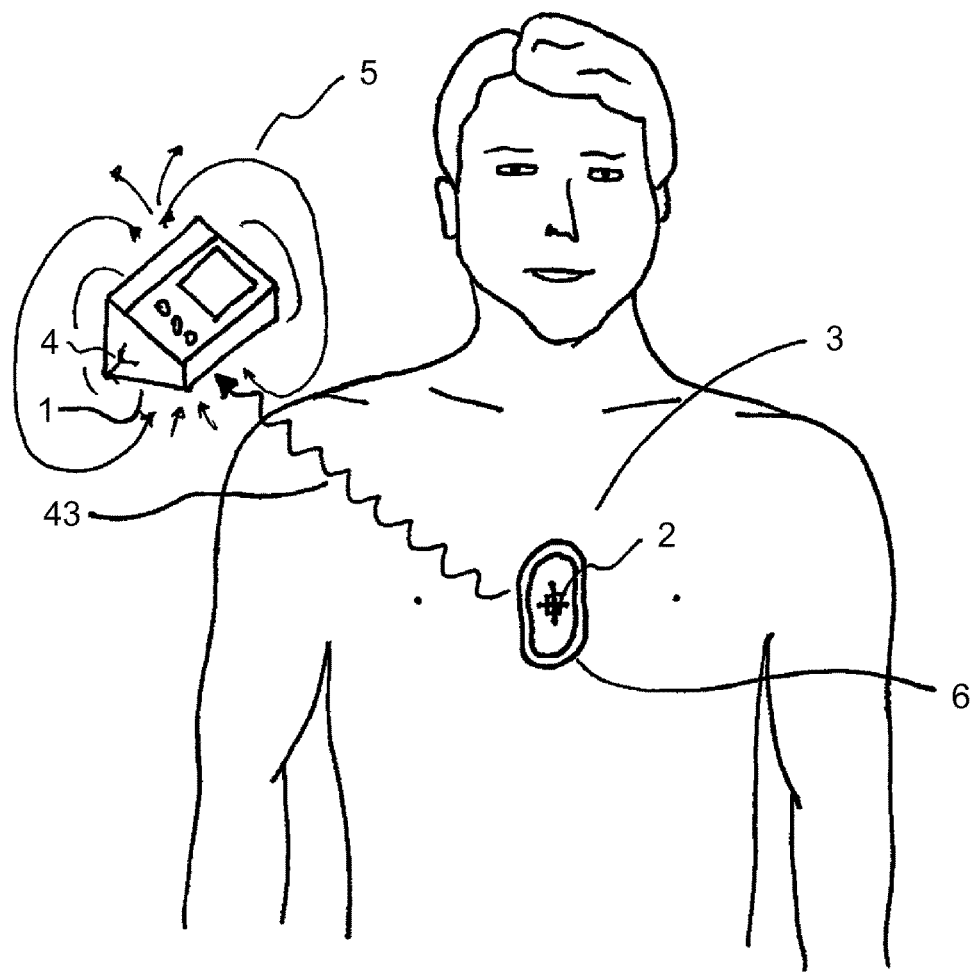
FIG. 17 is top view showing a wireless embodiment of the CPR assist device in which the field generator is not tethered to the fixed reference point containing the field detector.

In other embodiments, the sensor is not connected to the reference point and the device uses wireless technology as shown in the example of FIG. 17. In this example, the field detector is the position sensor 2, and the field generator is the reference sensor 4. The position sensor 2 may be placed on the chest of the patient 3, for example in a pad 6, and the reference sensor 4 may be positioned in a base unit 1, which may be a defibrillator. The reference sensor 4 generates a field 5 that is detected by the position sensor 2. The position sensor 2 may then send the response signal wirelessly 43 to the processor, and all of the signal processing may be performed by the processor within the base unit 1. The position sensor 2 on the patient's chest may be the field generator rather than the field detector. In this case, the position sensor may include the circuits necessary for generating the field, such as a waveform generator, amplifiers where suitable, and field generating coils. The position sensor may also include a wireless transmitter for sending synchronization signals to the reference sensor (in this case the field detector) and base unit. The synchronization signals may be used to coordinate the excitation of different coils, where the sensors include coils along different axes, as described above. The synchronization signals may also be used as the reference signal when processing the response signal. The synchronization signal may enable the processor to determine what combination of generator-detector is responsible for a given signal. The wireless signal from the position sensor may be detected by the reference sensor without the need for a wireless signal transmitter at the reference sensor.

Figure 18:
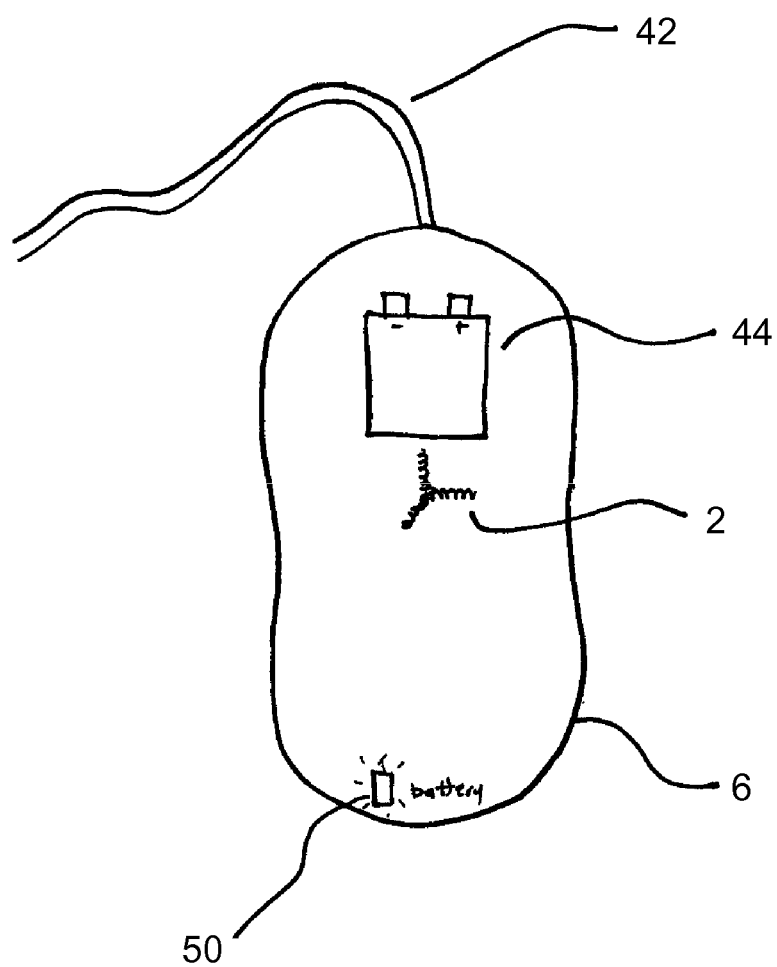
FIG. 18 is an illustration of an embodiment of the CPR assist device in the form of a pad or block to be placed on the patient's chest in which a battery or power source to power the CPR assist device is integrated into the pad or block.

In some embodiments, the CPR assist device may be completely powered from a battery in the reference sensor. If the reference sensor is provided in a base unit, for example a defibrillator, the entire device may be powered by the base unit's battery if the position sensor is connected to base unit. If the device is wireless, the field generator may have its own power supply integrated into it. Even if the sensors are connected to the base unit, auxiliary power sources may still be included with the sensors. For example, as shown in FIG. 18, an auxiliary battery source 44 may be placed inside the pad 6, or separately placed near the patient's chest. A battery light 50 may be provided to indicate the remaining battery life. In addition to the battery light 50, other feedback components may be provided with the pad 6.

Figure 19:
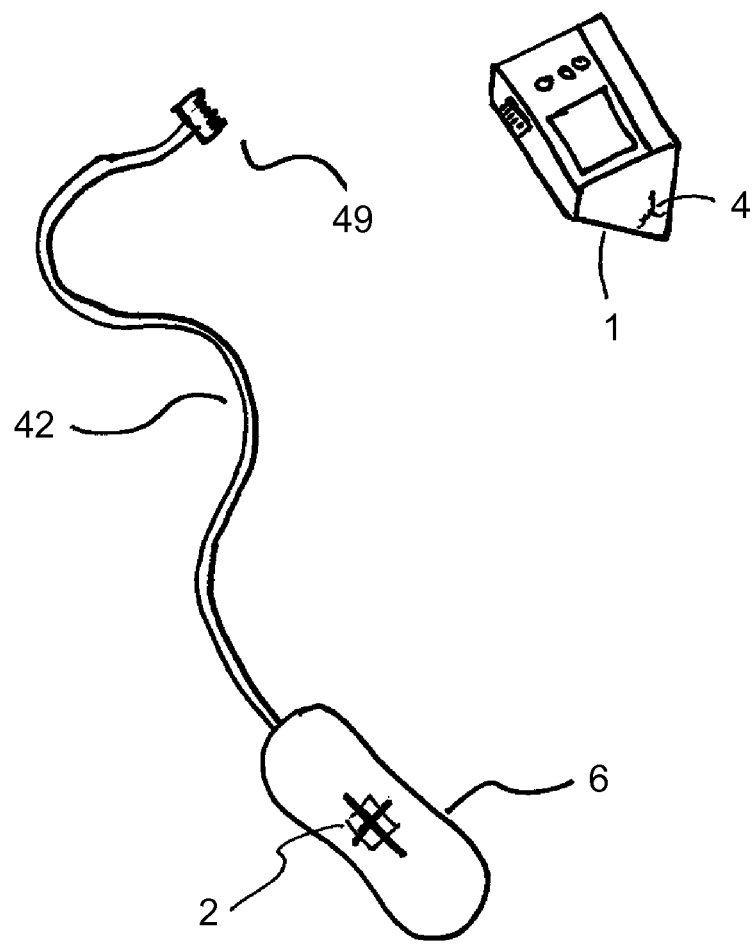
FIG. 19 is an illustration of a disposable embodiment of the CPR assist device in the form of a pad or block that is easily connected and disconnected from an external reference point.

In the example shown in FIG. 19, a connector 49 may allow the pad 6 to be easily disconnected from the base unit 1 and disposed or cleaned.

Where the device is integrated with a defibrillator, the position sensor may be integrated into the defibrillator pads. The battery to power any feedback components on the pad may also be integrated into the defibrillator pads so that it may be discarded with the pads after each use. This ensures that the feedback component does not draw any power from the defibrillator's main power source while allowing the pads and power source for the feedback component to be replaced all at once.

Although the present disclosure has focused primarily on the generation of AC sinusoidal electromagnetic fields, other embodiments may generate other field types or other signal types. In one embodiment, a pulsed DC signal may be used to modulate the field instead of a sinusoidal signal. The pulsed DC field consists of switching each field generating coil on and off so as to produce a pulsing electromagnetic field. A multiplexer may be used to select one of the three coils contained within the field generator and each coil may be activated sequentially. Alternatively, the generated fields may be frequency-multiplexed, as described above. By employing a DC modulating signal rather than a sinusoidal modulating signal, metallic distortion may be reduced. Specifically, the effect of conductive metals in the environment may be reduced by subduing or eliminating eddy current generation. Switching the coils on and off may prevent sustained eddy current generation and only a small eddy current may be produced on the rising edge of the DC pulse. The effect may be further mitigated by reducing the frequency of pulses. Despite reduced conductive metal distortion, the pulsed DC method may suffer from a lower possible sampling rate and a higher susceptibility to ferrous metals such as steel. Furthermore, a pulsed DC field may be contaminated by other DC electromagnetic fields such as the electromagnetic field of the Earth. As discussed above, other fields that may be generated include radiofrequency fields, sound fields, radiation fields, light fields, various modulated electromagnetic fields or any type of field that may be generated and detected. These fields may be similarly modulated in a variety of ways, as would be known to a person skilled in the art.

Figure 20:
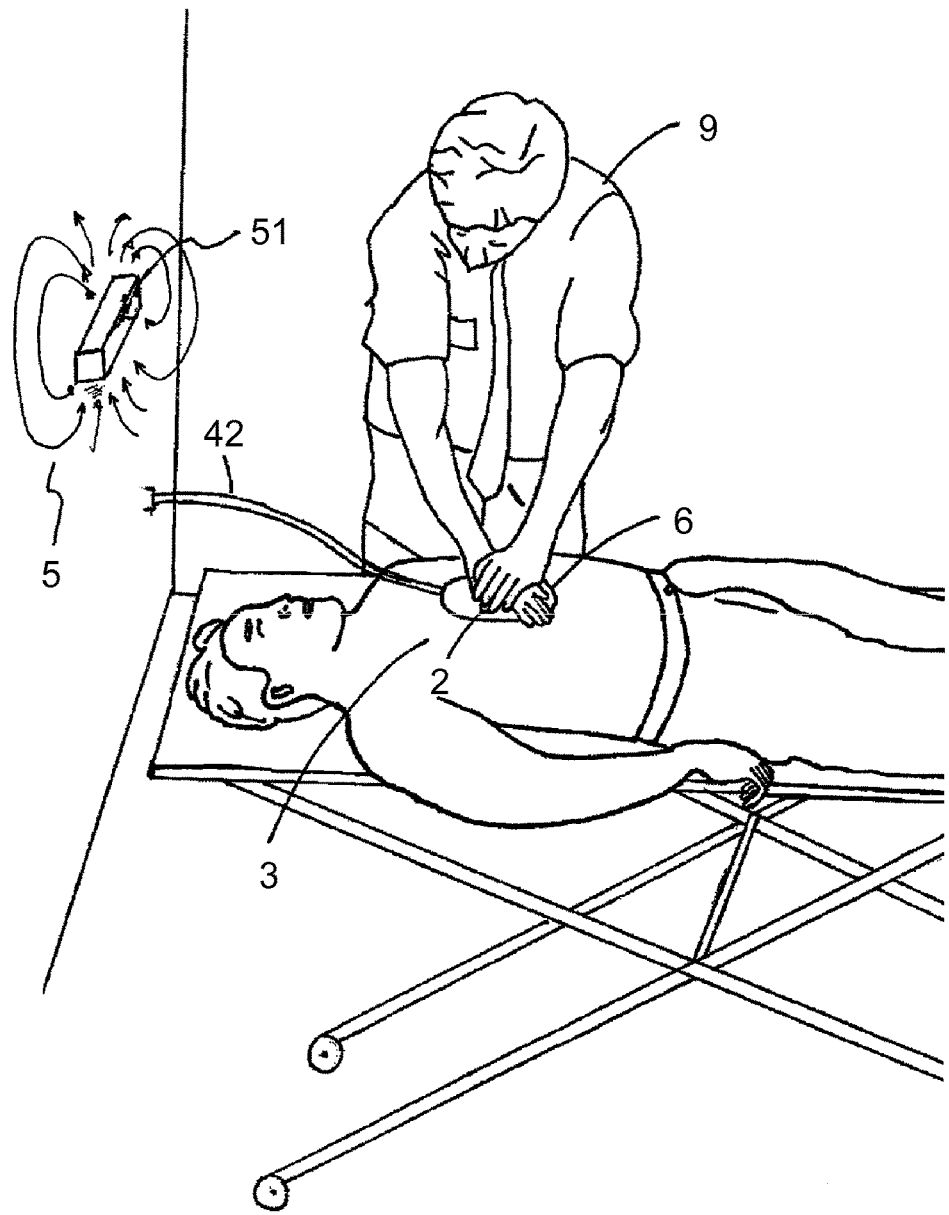
FIG. 20 is an illustration of a hospital room in which a reference point for an embodiment of the CPR assist device is installed on the wall.

The reference sensor may be installed in a number of convenient locations. FIG. 20 shows an example of the device used in a hospital room, in which the reference sensor may be placed on a hospital room wall 51, on the floor or on the ceiling. The reference sensor may be installed inside an ambulance on the wall or ceiling. It may also be installed on a moving gurney or hospital bed so that the reference sensor moves securely with the reference position which is the gurney. Furthermore, the reference sensor may be housed inside an AED case hanging on the wall in an airport, arena or other public location. If the reference sensor is permanently installed in a location, further calibration techniques may be applied so that the sensor is aware of its environment. This may help reduce the effects of ambient noise and metallic interference. This may help increase the effective range and accuracy of the generated field.

The device disclosed in this application may be capable of measuring other parameters related to CPR beyond chest compression depth. From the chest compression position information, chest compression rate may be calculated. As a chest compression reaches its maximum and minimum positions, a chest compression may be registered as an event. The number of these events per unit time may be calculated to determine compression rate. Effective CPR may be performed at a rate of 100 compressions per minute. Furthermore, chest recoil may be calculated by ensuring the chest of the patient is fully released after each compression. The position information may be used to determine if the distance that the chest is compressed is equivalent to the distance traveled by the chest during its release. The use of a fixed reference sensor makes this measurement more accurate compared to a measurement of this type using only accelerometers that may suffer from drift and may have no fixed reference. Proper hand position information during CPR may be determined using the present device. If the reference sensor is placed in a fixed known position, for example on the patient's anatomy, the position of the position sensor may be determined relative to the fixed reference sensor. Therefore, the present device may calculate if the distance between the sensors is appropriate. For example, effective CPR may be performed approximately two inches above the sternum of the patient. If the reference sensor is placed on the shoulder of the patient and the patient size is approximately known, hand position may be calculated as a desired distance and orientation of the position sensor from the reference sensor.

Figure 21:
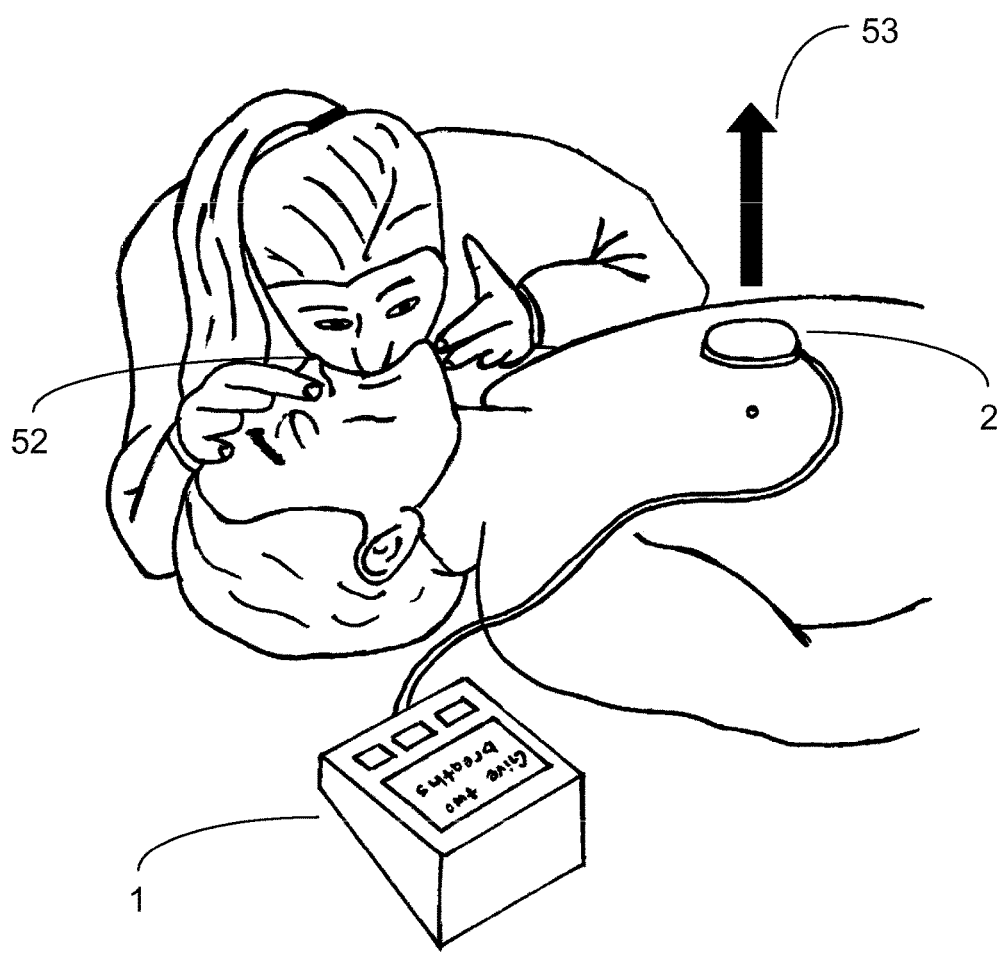
FIG. 21 is an illustration showing an embodiment of the CPR assist device being used to monitor and measure the effectiveness of rescue breathing in a CPR procedure.

As illustrated in the embodiment shown in FIG. 21, the position and reference sensors may also be used to determine and measure effective rescue breathing during CPR. Proper CPR often requires the administration of artificial breaths 52 to the victim to sustain proper oxygen levels in the blood. During CPR, proper administration of breaths is determined by visible chest rise 53. A position sensor affixed to the chest of the victim may be used to determine the position of the chest during rescue breathing. As a breath is properly administered, the victim's chest should rise and this rise may be determined by the position of the position sensor. Furthermore, proper electrode placement during defibrillation is vital to the success of the process. Position sensors embedded into the defibrillator electrode pads may be used to determine the relative position of the pads to each other as well as the absolute position of the pads relative to the base unit (e.g., a defibrillator). This information may be used to determine if the defibrillator pads have been properly placed on the victim.

Figure 22:
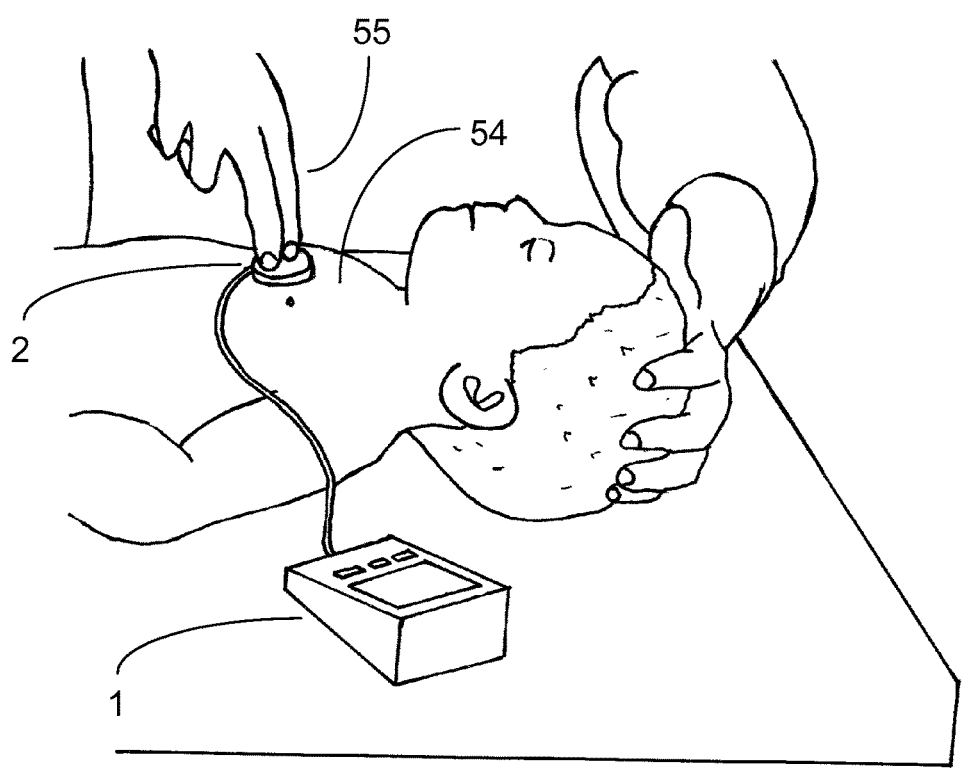
FIG. 22 is an illustration showing an embodiment of the CPR assist device being used to measure chest compression parameters during a CPR procedure on an infant.

The present device may also be used to assist in the administration of CPR on infants, for example as shown in the embodiment illustrated in FIG. 22, children and/or adults. For example, the position sensor 2 may be small and thin or otherwise suited to be placed on the chest of a small infant 54. The same position sensor may be used for an adult patient, or the position sensor may be specially adapted to suit infant CPR. For example, a pad housing the position sensor may be adapted to conform to the fingers of the rescuer as opposed to the hands, since effective infant CPR may be performed using only the fingers 55 of the rescuer instead of the entire hand. The position sensor may be designed to be lightweight and thin, to suit various types of CPR performed on various body sizes.

The technology and devices presented in this disclosure may be incorporated into a multitude of embodiments and configurations. For example, this device may be incorporated into a defibrillator in which CPR prompting and/or feedback is provided audibly, visually and/or tactilely using feedback components such as a display and speakers provided on the defibrillator. The present device may include a base unit, which may be portable, in which the reference sensor is located, and the base unit may be at a stationary location near the patient. The base unit may be incorporated into the defibrillator. The base unit may contain feedback components such as a display and a speaker to provide prompting and/or feedback to the rescuer. The base unit may itself act as storage for the device when not in use, for example as a first-aid kit box housing other first-aid supplies. The present device may also be incorporated into a device that fits entirely on the patient's chest in which one section of the device, containing the reference sensor, is attached to a stationary aspect of the patient's anatomy. The CPR assist device described alcove may also be integrated into a wearable CPR assist device, such as that described in U.S. patent application Ser. No. 11/936,184. The device described above may also be integrated into a CPR support device, such as that described in U.S. patent application Ser. No. 12/171,755.

There is also provided a method of measuring chest compression variables during administration of CPR using the above-described CPR assist device. The position of the position sensor is determined relative to the reference sensor. Based on this position information, chest compression variables such as compression depth, compression rate, and compression angle may be determined. This method may include providing feedback to the rescuer based on the determined compression variables.

Figure 23:
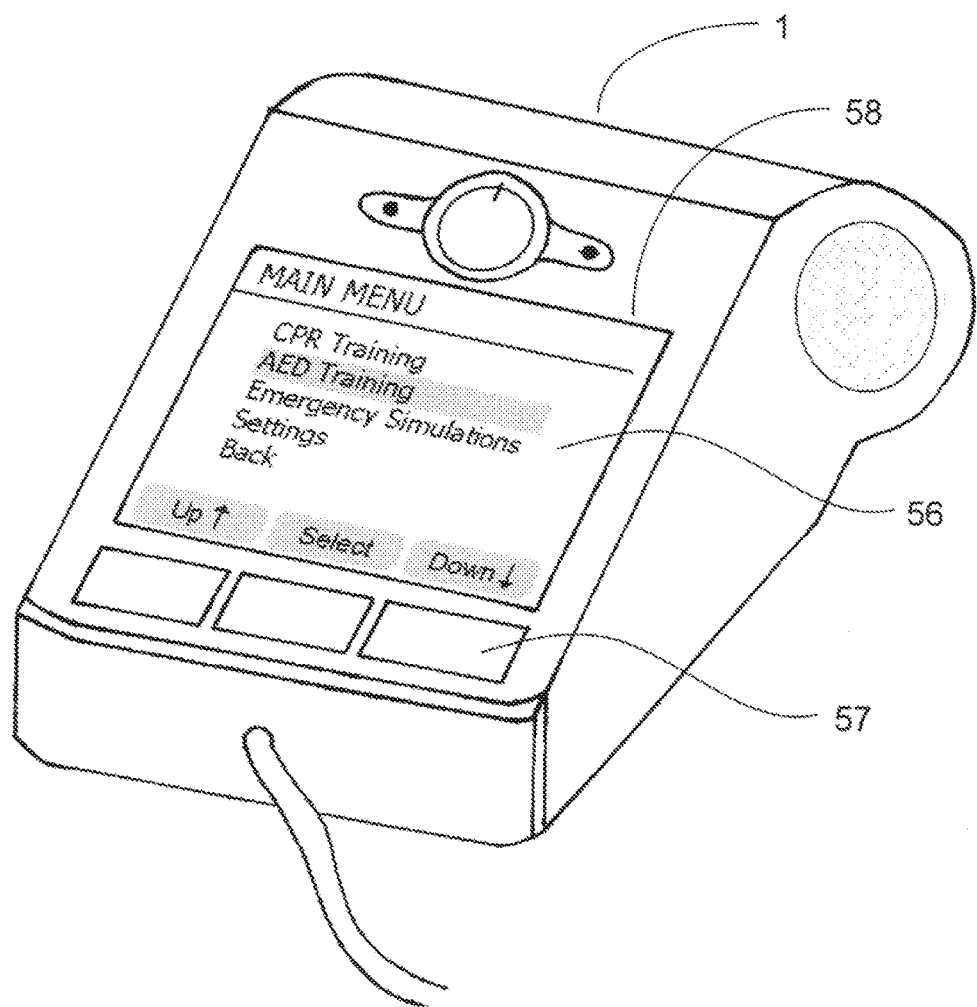
FIG. 23 is an illustration showing a base unit display suitable for use in CPR training.

As shown in the embodiment illustrated in FIG. 23, this device may also be used in a CPR training method, by storing the determined position information and calculated parameters, and analyzing this information. Menus 56 and buttons 57 provided on the device may allow the student or trainer to convert the emergency device into a training tool. Furthermore, the student or trainer may be able to select specific training scenarios contained within the device. The same device may be used for both training and actual emergency use. Alternatively, the device may be designed for dedicated emergency use only or dedicated training use only. Although not described in detail, it would be clear to a person skilled in the art that the information from the device may be uploaded into a separate computing device, such as a workstation, for further analysis. The information may be uploaded in real-time during a training session and feedback components on the device may provide real-time feedback to a student during a training session. Furthermore, the position sensor may be housed in an external, thin adhesive pad that may be placed on the chest of a CPR training manikin. Such a pad may maintain a realistic scenario for training in which no cumbersome blocks or other devices are used. In training, a position sensor may be directly incorporated into a manikin by either embedding it into the manikin's chest or affixing it to the manikin's chest in a permanent or temporary manner. Furthermore, the reference sensor may also be permanently or temporarily embedded into a stationary portion of the manikin such as the head, neck or legs. Such a system may be used to quickly and inexpensively retrofit existing training manikins so that the manikins may collect information on CPR performance and/or deliver objective CPR feedback and/or analysis during the training process.

Figure 24:
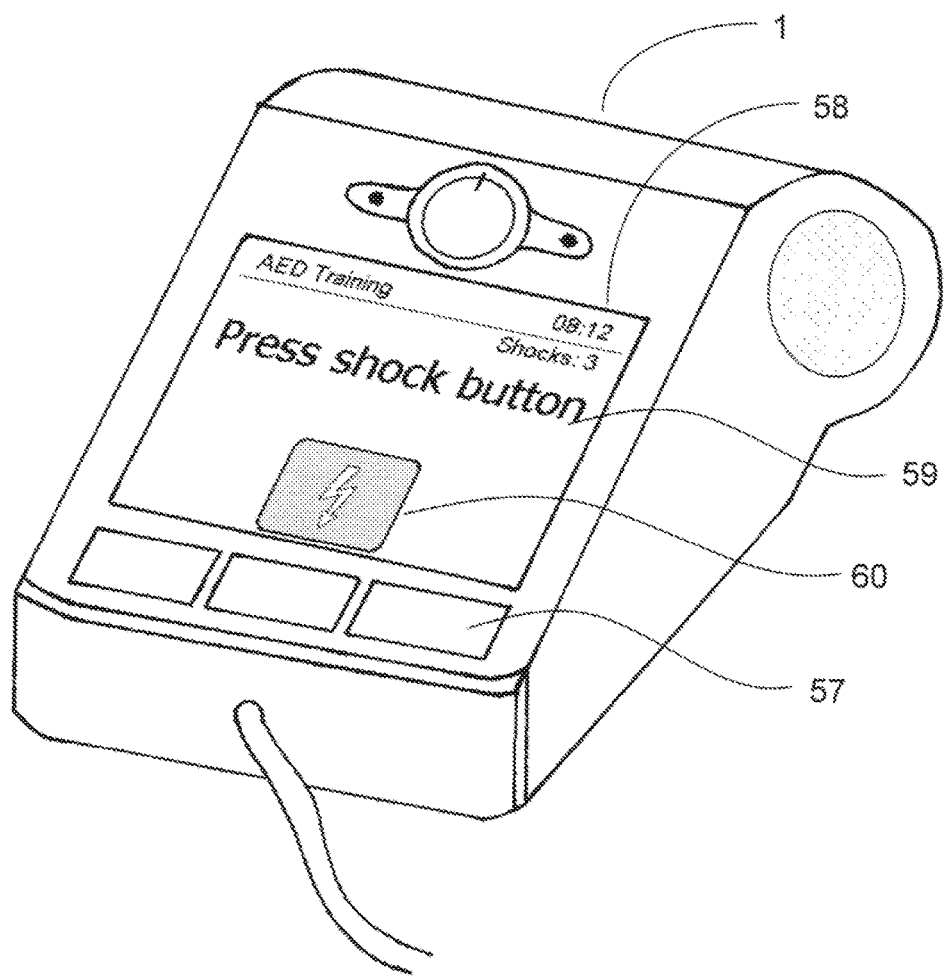
FIG. 24 is an illustration showing a base unit display suitable for use in automated external defibrillator (AED) training.

The device may also be suitable as an AED training unit, for example as shown in the embodiment illustrated in FIG. 24. The base station may serve as the AED unit and a display 58 integrated into the base unit may provide instructions 59 and lessons pertaining to the use of an AED. The display may show a shock button 60 similar to those found on AEDs and may guide a student through multiple AED simulations and scenarios. The device may be used as a combination AED and CPR training unit.

Although certain embodiments and examples have been provided in this disclosure, they are for the purpose of illustration only and are not intended to be limiting. A person skilled in the art would understand that variations may be possible. All references mentioned are hereby incorporated by reference in their entirety.

What is claimed is:

1. A device for determination of at least one compression parameter during administration of cardiopulmonary resuscitation (CPR) on a patient comprising:
    a position sensor including a field generator adapted to generate a field;
    a reference sensor including a field detector adapted to detect the field generated by the field generator and generate a response signal;
    wherein the field generator comprises at least one field generating coil and the field detector comprises at least one field detecting coil, and the generated field is an electromagnetic field,
    wherein at least one of the field generator and the field detector comprises at least three orthogonally wound field generating coils or field detecting coils, respectively,
    a defibrillator unit having two defibrillator pads;
    a processor adapted to determine, from the response signal, position and/or orientation information for the field detector relative to the field generator, to determine the at least one compression parameter using the determined position and/or orientation information of the field detector, the at least one compression parameter including a compression angle, and to determine whether a rescuer is administering CPR at an effective or desired compression angle to the patient's chest, the processor being provided in the defibrillator unit;
    wherein the position sensor is attached to or embedded in one of the two defibrillator pads which is configured to be placed on the patient's chest, and the reference sensor is attached to or embedded in the other of two defibrillator pads configured to be placed at a different location on the patient's chest;
    wherein the position sensor is adapted to move in accordance with the patient's chest and the reference sensor is adapted to be stationary relative to the patient, and
    wherein the position sensor is configured to determine a position of the one of the two defibrillator pads having the position sensor relative to the other of the two defibrillator pads having the reference sensor in order to determine if the rescuer is administering CPR at the effective or desired angle to the patient's chest and/or instruct the rescuer in maintaining the effective or desired compression angle.

2. The device of claim 1 wherein at least one of the field generator and the field detector comprises more than three coils.

3. The device of claim 1 wherein the field generator comprises at least two field generating coils, and each field generating coil sequentially generates a field detectable by the at least one field detecting coil.

4. The device of claim 1 wherein the field generator comprises at least two field generating coils and at least two field detecting coils, and each field generating coil generates a field at a different frequency, the field detector having at least one bandpass filter for separating the fields at different frequencies.

5. The device of claim 1 wherein the device comprises a feedback component configured to provide feedback to a CPR administrator based on the position information.

6. The device of claim 5 wherein the feedback comprises at least one of visual, audio, and tactile prompts.

7. The device of claim 1, wherein a power source is placed inside the one of the two defibrillator pads having the position sensor.

8. The device of claim 1 wherein the position information includes three-dimensional position information and orientation information.

9. The device of claim 8 wherein the position information includes position information in up to six degrees of freedom.

10. The device of claim 9 wherein the six degrees of freedom comprises x-axis position, y-axis position, z-axis position, roll, pitch and yaw.

11. The device of claim 1 wherein the generated field is detectable through an obstacle between the field generator and the field detector.

12. The device of claim 1 wherein the generated field is a sinusoidal modulated field or a pulsed DC signal modulated field.

13. The device of claim 1 wherein the position information is determined based on the strength of the response signal.

14. The device of claim 1 wherein the position information is determined by demodulating the response signal with a reference signal and smoothing the result.

15. The device of claim 1 wherein the at least one compression parameter further includes at least one of: a chest compression depth, a chest compression rate, and an extent of chest recoil.

16. The device of claim 1 wherein the processor is configured to perform filtering and signal conditioning on the detected field and corresponding response signal.

17. The device of claim 16 wherein the signal conditioning reduces effects of distortion in the response signal.

18. The device of claim 16 wherein signal filtering reduces external noise in the response signal.

19. The device of claim 1 wherein the position sensor and the reference sensor are connected by a wire or a cable.

20. The device of claim 1 wherein at least one of the position sensor and the reference sensor is wireless.

21. The device of claim 20 wherein the field detector is configured to detect the generated field wirelessly, the field detector being free of a wireless signal transmitter.

22. The device of claim 1 wherein the position sensor and the reference sensor are provided in a single unit adapted to be placed on the patient.

23. The device of claim 1 wherein the reference sensor is adapted to be located on a wall, a ceiling, a floor, a gurney, an ambulance, a helicopter, a moving vehicle, or a piece of external medical equipment.

24. The device of claim 1 wherein the position sensor comprises a pressure switch for measuring a least one of: the start of a compression, the end of a compression, the force of a compression, the pressure of a compression, the duration of a compression, the velocity of a compression and the frequency of compressions.

25. The device of claim 24 wherein at least one of the pressure of a compression, the force of a compression and the velocity of a compression is used to perform verifying the determined position information.

26. The device of claim 1 wherein the position sensor is adapted to be used with a variety of different patient body types.

27. The device of claim 26 wherein the position sensor is adapted to be used for administration of CPR on an infant.

28. The device of claim 1 wherein the position sensor is adapted to measure position of the patient's chest during rescue breathing for determination of the effective delivery of breaths.

29. The device of claim 1 wherein the position sensor is adapted to measure the placement of a CPR administrator's hands on the patient's chest.

30. The device of claim 1, wherein the reference sensor is provided in a base unit, and the position sensor is configured to be in communication with the base unit.

31. The device of claim 30, wherein the position sensor contains a wireless signal transmitter for sending a synchronization signal to the base unit and to the reference sensor, the synchronization signal being configured to coordinate the excitation of different field generating coils or different field detecting coils.

32. The device of claim 1, wherein the defibrillator unit is an automated external defibrillator (AED).

33. The device of claim 30, wherein a power source is provided in the base unit, and an auxiliary power source is provided with the position sensor.

34. The device of claim 30, wherein the base unit comprises a feedback component configured to provide feedback to a CPR administrator based on the position information.

35. The device of claim 34 wherein the feedback comprises at least one of visual, audio, and tactile prompts.

36. A device for determination of at least one compression parameter during administration of cardiopulmonary resuscitation (CPR) on a patient comprising:
    a reference sensor including a field generator adapted to generate a field;
    a position sensor including a field detector adapted to detect the field generated by the field generator and generate a response signal;
    wherein the field generator comprises at least one field generating coil and the field detector comprises at least one field detecting coil, and the generated field is an electromagnetic field,
    wherein at least one of the field generator and the field detector comprises at least three orthogonally wound field generating coils or field detecting coils, respectively,
    a defibrillator unit having two defibrillator pads;
    a processor adapted to determine, from the response signal, position and/or orientation information for the field detector relative to the field generator, to determine the at least one compression parameter using the determined position and/or orientation information of the field detector, the at least one compression parameter including a compression angle, and to determine whether a rescuer is administering CPR at an effective or desired compression angle to the patient's chest, the processor being provided in the defibrillator unit;

wherein the position sensor is attached to or embedded in one of the two defibrillator pads which is configured to be placed on the patient's chest, and the reference sensor is attached to or embedded in the other of two defibrillator pads configured to be placed at a different location on the patient's chest;

wherein the position sensor is adapted to move in accordance with the patient's chest and the reference sensor is adapted to be stationary relative to the patient, and wherein the position sensor is configured to determine a position of the one of the two defibrillator pads having the position sensor relative to the other of the two defibrillator pads having the reference sensor in order to determine if the rescuer is administering CPR at the effective or desired angle to the patient's chest and/or instruct the rescuer in maintaining the effective or desired compression angle.

37. The device of claim 36, wherein the field generator comprises at least two field generating coils and at least two field detecting coils, and each field generating coil generates a field at a different frequency, the field detector having at least one bandpass filter for separating the fields at different frequencies.

38. The device of claim 36, wherein the device comprises a feedback component configured to provide feedback to a CPR administrator based on the position information.

39. The device of claim 36, wherein the position information includes three-dimensional position information and orientation information, the position information including position information in up to six degrees of freedom.

40. The device of claim 36, wherein the position sensor comprises a pressure switch for measuring a least one of: the start of a compression, the end of a compression, the force of a compression, the pressure of a compression, the duration of a compression, the velocity of a compression and the frequency of compressions.

41. The device of claim 36, wherein the defibrillator unit is an automated external defibrillator (AED).

* * * * *